(12) United States Patent
Miraki et al.

(10) Patent No.: US 9,592,047 B2
(45) Date of Patent: Mar. 14, 2017

(54) SYSTEM FOR SECURING SUTURES

(71) Applicant: Edwards Lifesciences Corporation, Irvine, CA (US)

(72) Inventors: Manouchehr A. Miraki, Laguna Hills, CA (US); Kevin Dang, Garden Grove, CA (US); Yoon H. Kwon, Mission Viejo, CA (US); William Biller, Tustin, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 192 days.

(21) Appl. No.: 14/133,040

(22) Filed: Dec. 18, 2013

(65) Prior Publication Data

US 2014/0180337 A1 Jun. 26, 2014

Related U.S. Application Data

(60) Provisional application No. 61/740,769, filed on Dec. 21, 2012.

(51) Int. Cl.
  A61B 17/04 (2006.01)
  A61B 17/00 (2006.01)
  A61B 17/06 (2006.01)

(52) U.S. Cl.
  CPC ...... *A61B 17/0487* (2013.01); *A61B 17/0467* (2013.01); *A61B 2017/00084* (2013.01); *A61B 2017/0488* (2013.01); *A61B 2017/0619* (2013.01); *A61B 2217/007* (2013.01)

(58) Field of Classification Search
  CPC .... A61B 2017/0446; A61B 2017/0454; A61B 2017/0451; A61B 2017/0487; A61B 2017/0488; A61B 2017/0489; A61B 17/0487; A61B 17/0467

USPC ................ 606/142, 148, 144, 228, 214, 232
See application file for complete search history.

(56) References Cited

U.S. PATENT DOCUMENTS

| | | | |
|---|---|---|---|
| 2,264,679 A | 12/1941 | Ravel | |
| 2,516,710 A | 7/1950 | Mascolo | |
| 2,715,486 A | 8/1955 | Marcoff-Moghadam et al. | |
| 2,890,519 A | 6/1959 | Storz, Jr. | |
| 3,143,742 A | 8/1964 | Cromie | |
| 3,249,104 A | 5/1966 | Hohnstein | |
| 3,274,658 A | 9/1966 | Pile | |
| 3,452,742 A | 7/1969 | Muller | |
| 3,506,012 A | 4/1970 | Brown | |
| 3,509,882 A | 5/1970 | Blake | |

(Continued)

FOREIGN PATENT DOCUMENTS

WO 0187165 A1 11/2001
WO 2010006448 A1 1/2010

OTHER PUBLICATIONS

Supplementary Partial Search Report for EP13866223, completed Jul. 29, 2016.

*Primary Examiner* — Tuan V Nguyen
(74) *Attorney, Agent, or Firm* — Klarquist Sparkman, LLP

(57) ABSTRACT

Described herein are systems and methods for securing sutures that obviate the need for tying knots. Instead of tying two ends of a suture or two sutures together with a knot, two or more suture portions can be fused or cauterized together using heat. A device can be applied to adjacent suture portions that heats the suture portions and causes the suture portions to fuse together, effectively securing the suture portions together without a knot.

22 Claims, 21 Drawing Sheets

(56) References Cited

U.S. PATENT DOCUMENTS

| | | |
|---|---|---|
| 3,513,848 A | 5/1970 | Winston |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,958,576 A | 5/1976 | Komiya |
| 3,976,079 A | 8/1976 | Samuels et al. |
| 3,996,623 A | 12/1976 | Kaster |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,549,545 A | 10/1985 | Levy |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk et al. |
| RE34,021 E | 8/1992 | Mueller et al. |
| 5,152,769 A | 10/1992 | Baber |
| 5,154,189 A | 10/1992 | Oberlander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,236,440 A | 8/1993 | Hlavacek |
| 5,242,456 A | 9/1993 | Nash et al. |
| 5,246,443 A | 9/1993 | Mai |
| 5,258,011 A | 11/1993 | Drews |
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,290 A | 4/1994 | Martins et al. |
| 5,306,296 A | 4/1994 | Wright et al. |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,383,904 A | 1/1995 | Totakura et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,561 A | 10/1995 | Voda |
| 5,474,557 A | 12/1995 | Mai |
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,630,824 A | 5/1997 | Hart |
| 5,632,752 A | 5/1997 | Buelna |
| 5,632,753 A | 5/1997 | Loeser |
| 5,643,295 A | 7/1997 | Yoon |
| 5,645,568 A | 7/1997 | Chervitz et al. |
| 5,665,109 A | 9/1997 | Yoon |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |

(56) References Cited

U.S. PATENT DOCUMENTS

| | | | |
|---|---|---|---|
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,849,019 A | 12/1998 | Yoon |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,394 A | 4/1999 | Kienzle et al. |
| 5,919,207 A | 7/1999 | Taheri |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,066,160 A | 5/2000 | Colvin et al. |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,174,324 B1 * | 1/2001 | Egan ............... A61B 17/0487 |
| | | 156/73.1 |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,217,591 B1 | 4/2001 | Egan et al. |
| 6,254,615 B1 | 7/2001 | Bolduc et al. |
| 6,306,141 B1 | 10/2001 | Jervis |
| 6,346,112 B2 | 2/2002 | Adams |
| 6,368,343 B1 | 4/2002 | Bonutti et al. |
| 6,409,743 B1 * | 6/2002 | Fenton, Jr. ......... A61B 17/0487 |
| | | 606/232 |
| 6,514,265 B2 | 2/2003 | Ho et al. |
| 6,551,332 B1 | 4/2003 | Nguyen et al. |
| 6,607,541 B1 | 8/2003 | Gardiner et al. |
| 6,613,059 B2 | 9/2003 | Schaller et al. |
| 6,641,593 B1 | 11/2003 | Schaller et al. |
| 6,682,540 B1 | 1/2004 | Sancoff et al. |
| 6,749,622 B2 | 6/2004 | McGuckin, Jr. et al. |
| 6,776,784 B2 | 8/2004 | Ginn |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,147,652 B2 | 12/2006 | Bonutti et al. |
| 2004/0044366 A1 * | 3/2004 | Bonutti ............. A61B 17/0487 |
| | | 606/232 |
| 2004/0087974 A1 * | 5/2004 | Bittar ................. A61B 17/0469 |
| | | 606/139 |
| 2004/0122451 A1 | 6/2004 | Wood |
| 2004/0260344 A1 * | 12/2004 | Lyons ............... A61B 17/0487 |
| | | 606/232 |
| 2006/0047314 A1 | 3/2006 | Green |
| 2010/0049218 A1 | 2/2010 | Miyamoto et al. |
| 2012/0165865 A1 * | 6/2012 | Fujisaki ............. A61B 17/0487 |
| | | 606/232 |
| 2012/0197296 A1 | 8/2012 | Mayer et al. |
| 2013/0231701 A1 * | 9/2013 | Voss ................. A61B 17/0057 |
| | | 606/232 |

* cited by examiner

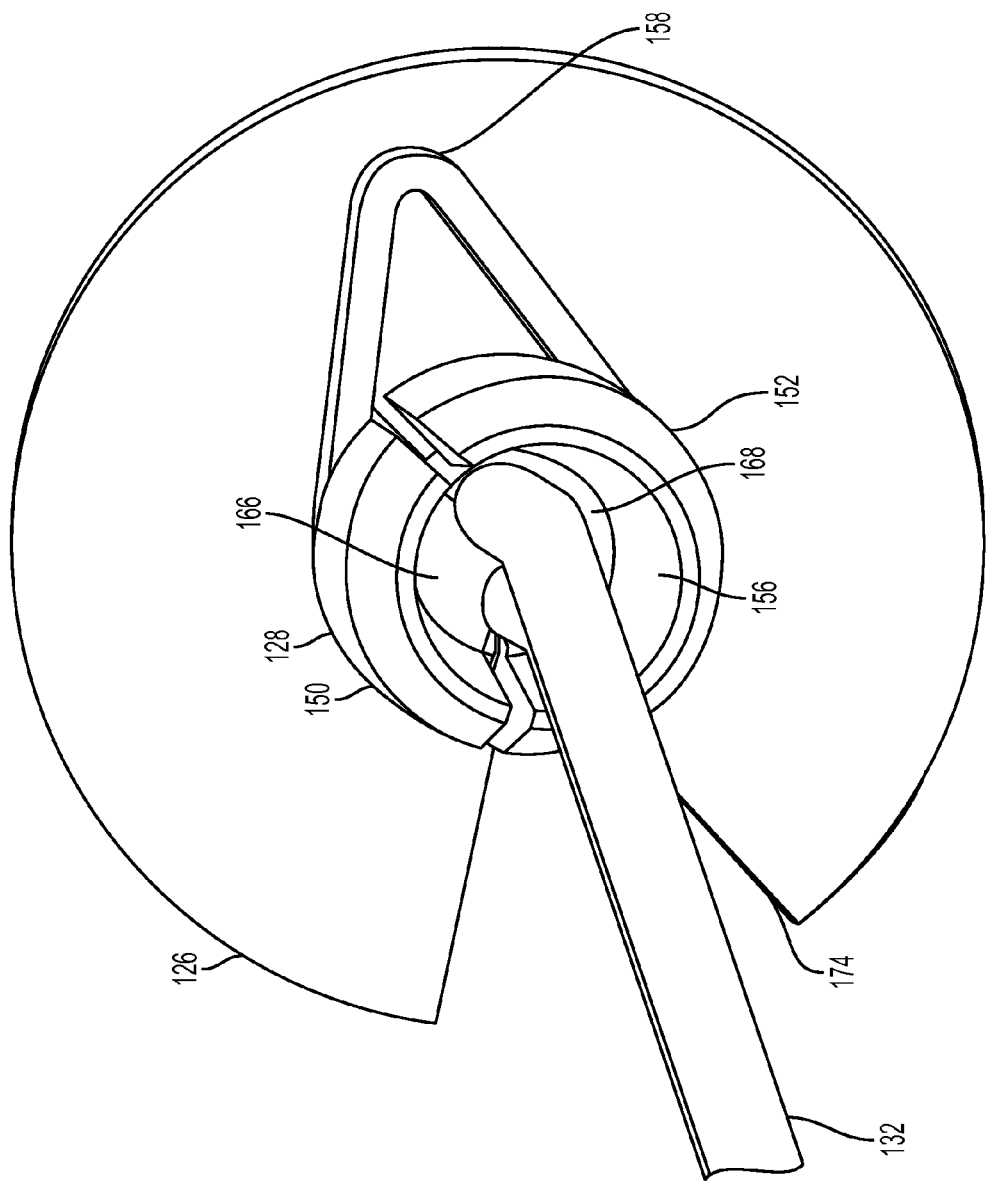

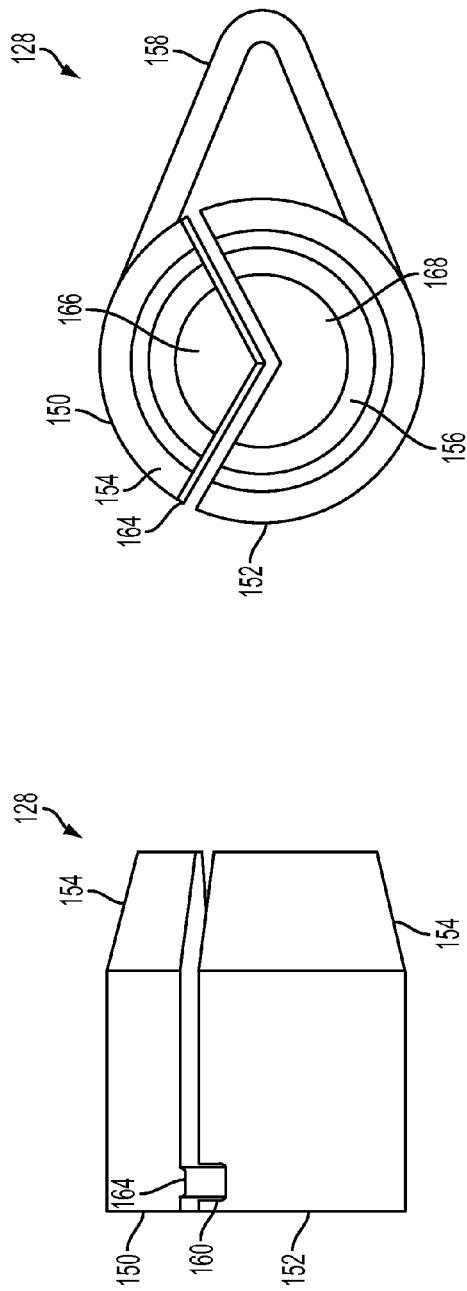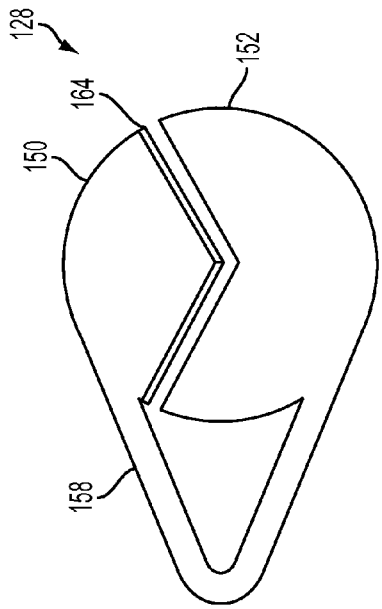

SYSTEM FOR SECURING SUTURES

CROSS REFERENCE TO RELATED APPLICATION

The application claims the benefit of U.S. Provisional Patent Application No. 61/740,769 filed on Dec. 21, 2012, which is herein incorporated by reference.

FIELD

This disclosure is related to devices and methods for securing surgical sutures.

BACKGROUND

Surgically placed sutures are frequently used in many different surgical procedures. Exemplary procedures include closing an open section of blood vessel to secure placement of tubes for cardiopulmonary bypass and implantation of a prosthetic device within the heart. In such procedures, different suture types and suture patterns are often used, such as purse string sutures, mattress sutures, running sutures, and others. Conventionally, at the end of such a procedure, the two free ends of each suture are tied together in a knot to secure the suture in place.

SUMMARY

Described herein are systems and methods for securing sutures that obviate the need for tying knots. Instead of tying two ends of a suture or two suture portions together with a knot, two or more suture portions can be fused or cauterized together using heat. A device can be applied to adjacent suture portions that heats the suture portions and causes the suture portions to fuse together, effectively securing the suture portions together.

Some embodiments of a suture securement device comprise a handle, an elongated outer shaft having a proximal end portion coupled to the handle and a distal end portion opposite the proximal end, an inner shaft movable proximally and distally within the outer shaft, an electrical heating element positioned within the outer shaft, and a suture holder at the distal end portion of the outer shaft. The suture holder can has an open position and a closed position, wherein in the open position the suture holder is configured to receive sutures, and in the closed position the suture holder is configured to hold sutures and prevent longitudinal movement of held sutures relative to the outer shaft. Actuation of the device causes the inner shaft and the heating element to move distally relative to the outer shaft and the suture holder, such that the distal end portion of the inner shaft causes the suture holder to move from the open position to the closed position, and such that the heating element moves into the proximity of the suture holder to fuse together sutures held by the suture holder.

In some embodiments, the suture holder comprises a first portion and a second portion that are hingedly coupled together for articulation between the open position and the closed position, such as in a clamshell-type configuration. The first and second portions of the suture holder can be coupled by an elastically flexible hinge that biases the first and second portions toward the open position, such that the suture holder releases the fused sutures when the inner shaft moves proximally off of the suture holder. The first portion of the suture holder can be fixed relative to the outer shaft and a second portion of the suture holder can move between the open position and the closed position. In other embodiments, both portions of the suture holder can move. In some embodiments, the suture holder has a sloped proximal surface and the inner shaft has a sloped distal surface, and contact between the sloped proximal surface and the sloped distal surface causes the suture holder to close. In some embodiments, the suture holder comprises a proximal recess and the heating element moves at least partially into the proximal recess, such as to both fuse the sutures and to cut off free ends of the sutures.

In some embodiments, the device can comprise an electrical power source in the handle that is electrically coupled to the heating element. In other embodiments, the device can be electrically coupled to an electrical power source.

In some embodiments, the outer shaft comprises a longitudinal slot at the distal end portion of the outer shaft and, in the open position, free ends of sutures received by the suture holder extend out of the device through the slot to allow manual tensioning of the sutures. In some embodiments, the inner shaft comprises a longitudinal slot at the distal end portion of the inner shaft and, in the closed position, free ends of sutures held by the suture holder extend out of the device through the slots in the inner and outer shafts.

In some embodiments, the heating element is positioned within the inner shaft and the inner shaft comprises at least two radial openings adjacent to the heating element to vent heat from the heating element.

In some embodiments, the device includes a suture collar at the distal end of the outer shaft. The suture collar can comprise a central opening for collaring sutures received by the suture holder, and a lateral gate that allows sutures to enter laterally into the central opening in a radially inward direction through the lateral gate, and the lateral gate blocks sutures from exiting the central opening in a radially outward direction. A stationary part of the suture holder can be fixed to a proximal side of a suture collar. The outer shaft can include a slot extending proximally from a distal end of the outer shaft, and the slot can be circumferentially aligned with the lateral gate in the suture collar and a lateral opening in the suture holder such that an intermediate portion of a suture can be laterally inserted through the slot and through the lateral gate and into the central opening and into the suture holder.

Some embodiments of a suture securement device comprise a handle, an elongated outer shaft having a proximal end portion coupled to the handle and a distal end portion opposite the proximal end, an electrical heating element positioned within the outer shaft, and a suture collar at the distal end portion of the outer shaft. The suture collar has a central opening for collaring sutures and a lateral gate that allows an intermediate portion of a suture to enter laterally into the central opening in a radially inward direction through the lateral gate, and the gate blocks sutures from exiting the central opening in a radially outward direction. Actuation of the device causes the heating element to fuse together sutures collared by the suture collar.

In some embodiments, the suture collar is generally disk-shaped and further comprises a generally wedge-shaped slot extending radially from a radially outer perimeter of the suture collar to the lateral gate. In some embodiments, the lateral gate comprises an elastically flexible flap that deflects to allow sutures to pass into the central opening, such that a radially inward force from a suture causes the flap to elastically deflect into the central opening to open the lateral gate.

In some embodiments, the device further comprises an air conduit extending from the handle to the distal end portion of the outer shaft and configured to conduct air to the distal end portion to help cool the heating element and/or the fused sutures. The air conduit can be coupled to a pump in the handle or to an external air supply source.

The foregoing and other objects, features, and advantages of this disclosure will become more apparent from the following detailed description, which proceeds with reference to the accompanying figures.

BRIEF DESCRIPTION OF THE DRAWINGS

FIG. 22 is a perspective view from a proximal end of a suture holder and a suture collar of the device of FIG. 12 in the closed position, with other portions of the device not shown.

FIG. 23-25 are side, proximal end, and distal end views, respectively, of an exemplary suture holder of the device of FIG. 12.

DETAILED DESCRIPTION

Described herein are systems and methods for securing sutures that obviate the need for tying knots. Instead of tying two ends of a suture or two or more sutures together with a knot, the suture portions can be fused or cauterized together using heat. A device can be applied to two or more adjacent suture portions that heats the suture portions and causes the suture portions to fuse together, effectively securing the suture portions together.

While this disclosure primarily describes securing two suture portions together, embodiments of the disclosed systems and methods can also be used to secure three or more suture portions together in a similar matter. The two suture portions being secured together can be two portions of the same suture (e.g., opposite ends) or portions of two different sutures. Furthermore, the suture portions secured together can be any portion along a length of a suture, such as an end of the suture or a portion of the suture between its ends.

The disclosed systems and methods can be used with any type of sutures that are capable of being fused or cauterized together when heat is applied. Exemplary suture materials can comprise biological tissues (e.g., collagen-based tissue), polyglycolide, polydioxanone, polyester, nylon, polypropylene, and other polymeric materials. Some sutures comprise several strands of fibers braided or woven together.

Figure 1:
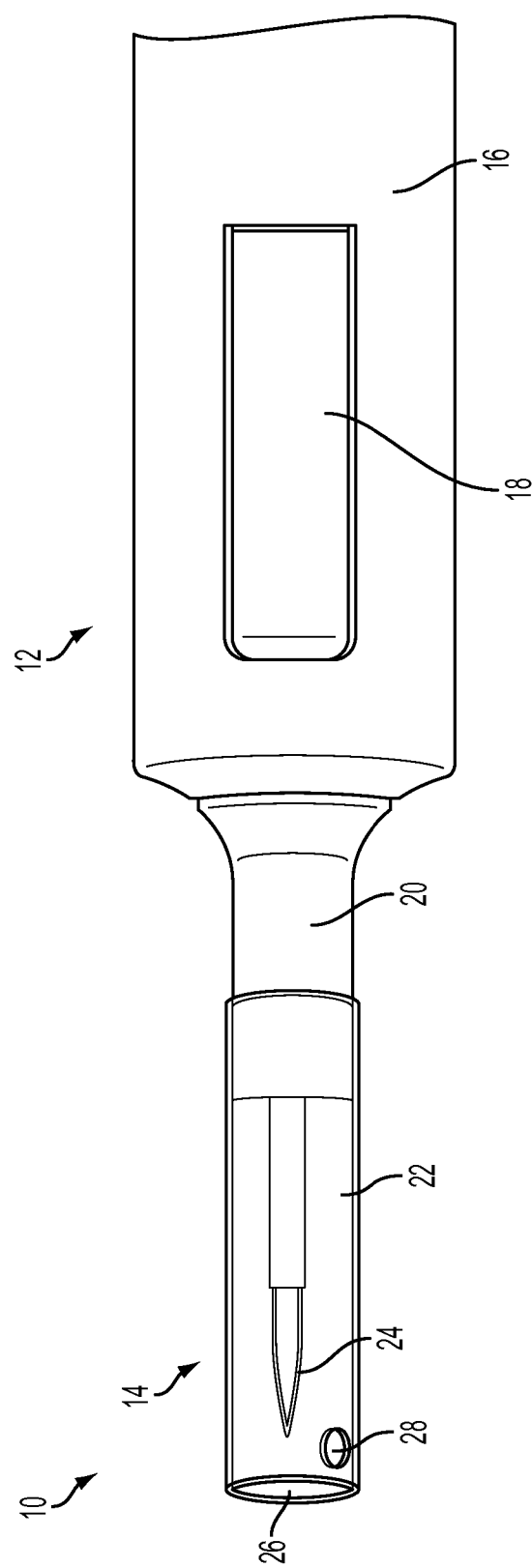
FIG. 1 is a top view of an exemplary suture securement device disclosed herein.

FIG. 1 shows a portion of an exemplary device 10 that is configured to fuse sutures together using heat. The device 10 comprises a handle portion 12 that a user holds to operate the device and a distal portion 14 configured to apply heat to sutures to fuse them together. The handle portion 12 can comprise a generally cylindrical body 16 and an actuator 18. The body 16 can house additional components, such as electronics and/or a power supply (e.g., one or more batteries). The actuator 18 can comprise an electrical switch, a knob, a dial, a button, or other control mechanism. The handle portion 12 can be coupled to a remote power source in some embodiments.

Figure 2:
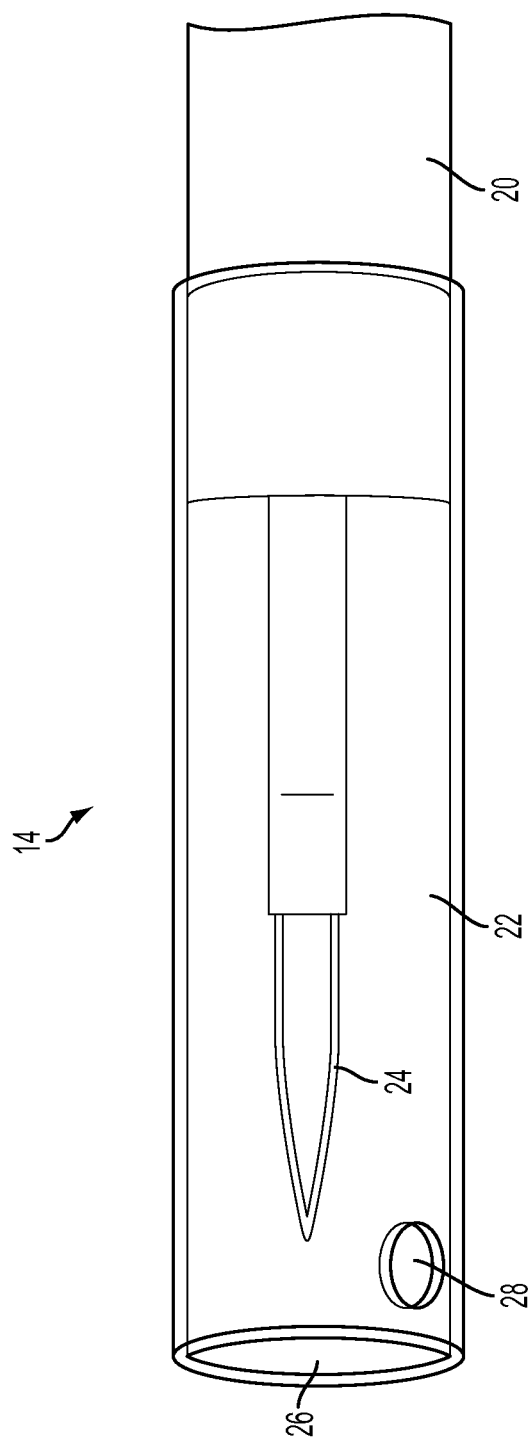
FIG. 2 is a top view of another exemplary suture securement device disclosed herein.

As shown in FIG. 2, the distal portion 14 can comprise an extension portion 20 of the body 16 that has a reduced width than the body, an electrical heating element 24 extending distally from the extension portion 20, and a sheath 22 that extends from the extension portion 20 and surrounds the heating element 24. The sheath 22 can be generally cylindrical and can have a distal opening 26 positioned a small distance distally from a distal end of the heating element 24. The sheath 22 can also have a lateral opening 28 in a sidewall of the sheath adjacent to the distal end of the heating element 24.

The heating element 24 can comprise a loop of wire or filament that heats when an electrical current passes through it. The distal end of the heating element 24 can comprise various shapes, such as an eyelet shape through which sutures can pass, or a crescent shape configured to curve around sutures.

In some embodiments, the heating element 24 can be axially, rotationally, and/or radially moveable relative to the sheath 22. For example, in some embodiments, the heating element can be retracted proximally within the sheath 22 while sutures are guided into or through the sheath, and then advanced distally relative to the sheath 22 in order to cause the heating element to contact the sutures. In some embodiments, the heating element 24 can be moved radially within the sheath to contact the sutures. In some embodiments, the heating element can comprise two or more loops and the sutures can be positioned between the loops. In other embodiments, the heating element 24 can be fixed axially relative to the sheath 22.

Figure 3:
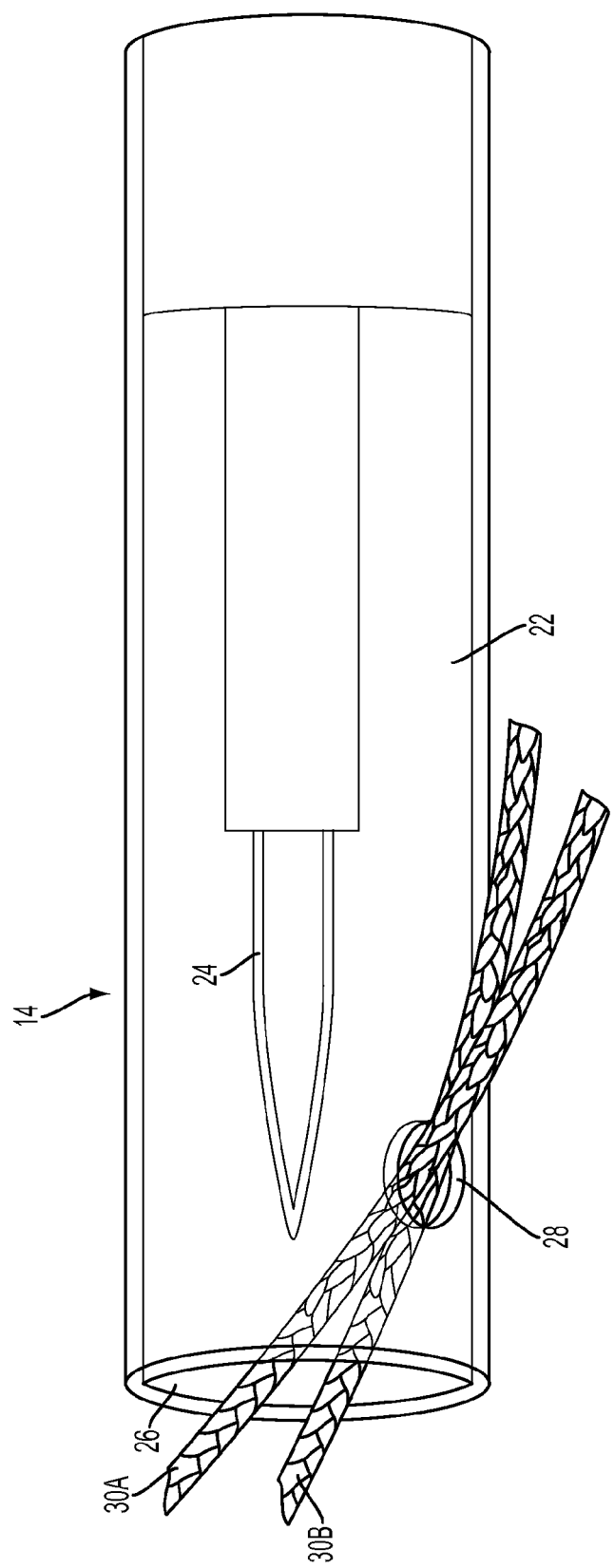
FIG. 3 is a top view of yet another exemplary suture securement device disclosed herein.

In use, two or more suture portions 30A and 30B can be threaded through the distal opening 26 and out through the lateral opening 28 such that the suture portions pass adjacent to the heating element 24, as shown in FIG. 3. Typically, the two suture portions 30A, 30B are projecting from a surgical location in the body, and so the device 10 is moved in conjunction with the suture portions to guide the suture portions through the openings 26 and 28 in the sheath 22. In some cases, two suture ends can be introduced into the sheath 22 through the distal opening 26 without extending out through the lateral opening 28, such that the ends of the sutures can be fused together.

The distal portion 14 can be advanced along or over the suture portions until a desired fusing location along the suture portions is adjacent to the heating element 24. In some cases, this can include advancing the distal portion 14 until the distal end of the sheath 22 contacts the tissue or other object from which the suture portions are protruding. In some methods, the free ends of the suture portions 30A, 30B that extend out from the lateral opening 28 in the sheath can be grasped and pulled to a desired tension, using the distal end of the sheath 22 to hold the surrounding tissue or material steady as the sutures are pulled taught.

Figure 4:
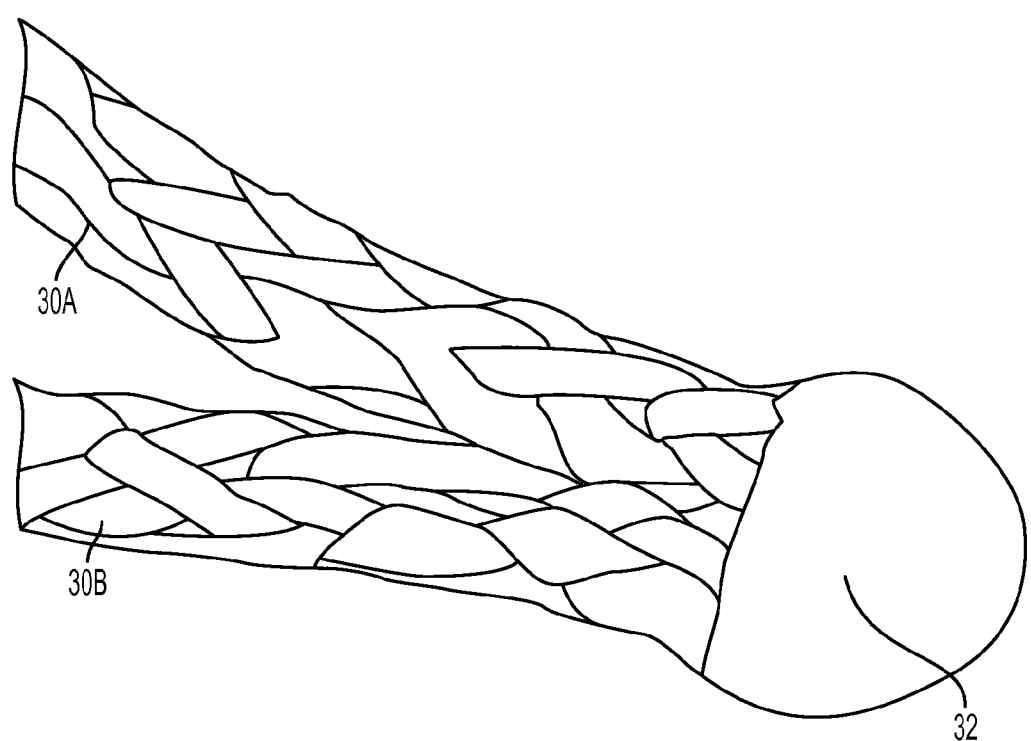
FIG. 4 shows two sutures fused together.

When the distal portion is at the desired location along the suture portions 30A, 30B such that the sections to be fused are adjacent the heating element 24 and/or the desired tension applied to the suture portions, the user can actuate the actuator 18, which can cause the heating element 24 to advance distally within the sheath 22 and into contact with the sutures and/or can cause an electrical current to flow through the heating element 24 and increase the temperature of the heating element. In some embodiments, two or more different actuators are included to separately control movement of the heating element and heating of the heating element. When the heating element is heated sufficiently, the sections of the suture portions 30A, 30B that are adjacent to or in direct contact with the heating element are heated and fused together. The fusing of the suture portions can include melting and/or cauterization of the suture material such that the material of two suture portions meld together to form a connection 32, as shown in FIG. 4. In some embodiments, the fusing of the suture portions causes the end portions of the sutures beyond the connection 32 to be severed off, leaving the connection 32 at the ends of the sutures, as shown in FIG. 4. In other embodiments, the end portions of the sutures beyond the connection 32 can be manually cut off. The tissue is protected from the heating element 24 because the distal end of the sheath 22 remains positioned distal to the distal end of the heating element when the heating element is actuated. The sheath 22 also protects the tissue laterally from contacting the heating element.

After the sutures are fused, the device 10 can be removed and optionally used to fuse addition suture portions by repeating the methods described herein. In some embodiments, the device 10 can be reused for more than one surgery, while other embodiments can be disposable after a single surgery. In some embodiments, the distal sheath 22 and/or the heating element 24, or the entire distal portion 14 can be removed, disposed, and replaced between surgeries.

Figure 5:
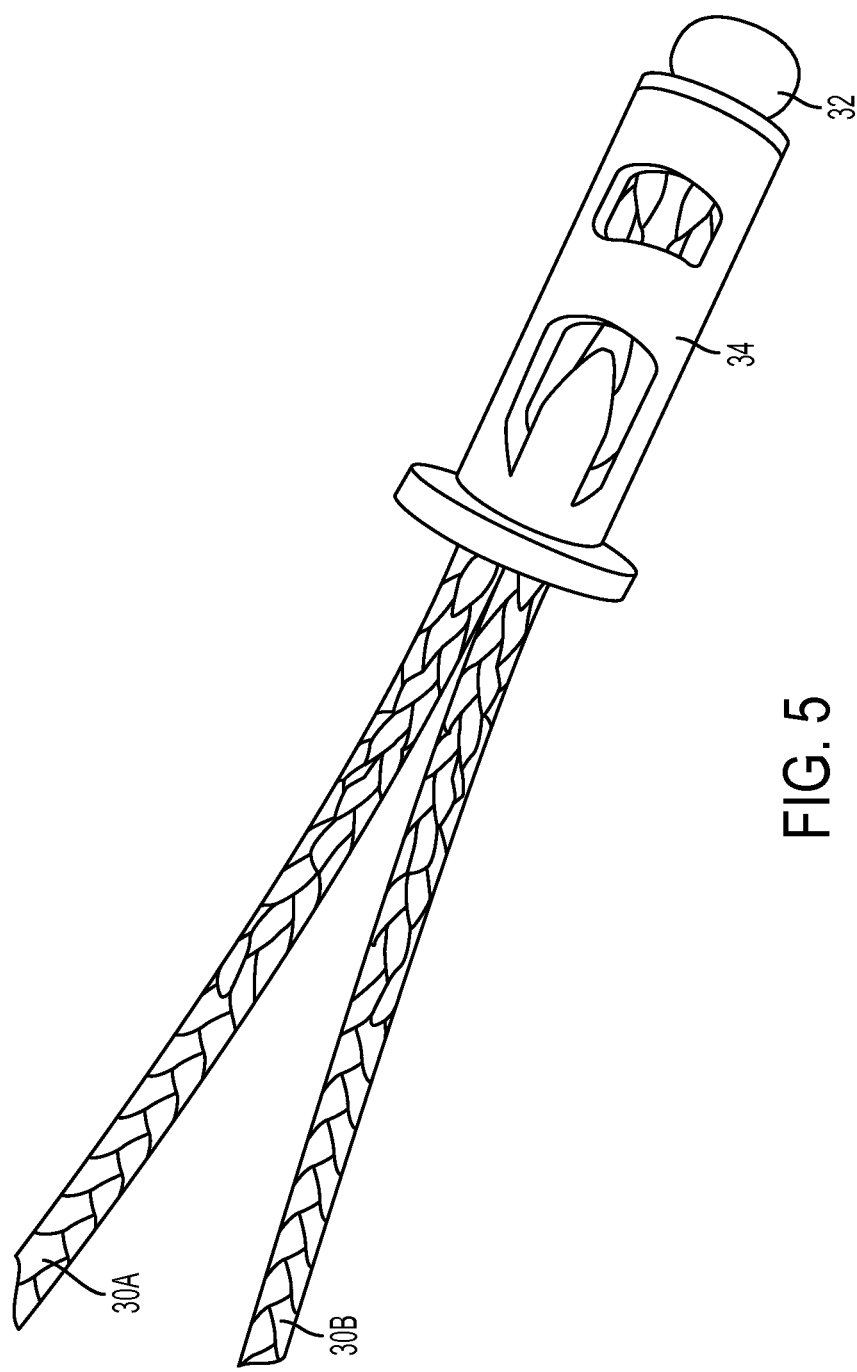
FIG. 5 shows two sutures secured together with an exemplary clip disclosed herein.
Figure 6:
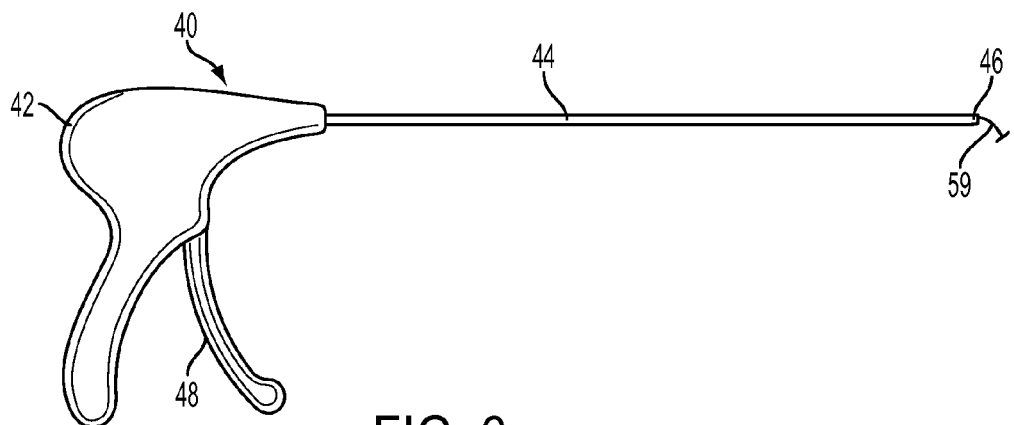
FIG. 6 is a side view of still another exemplary suture securement device disclosed herein.

In some embodiments, a heat-based suture fusing device, like those described herein, can be included as part of a suture clip deployment device, such as the suture clip deployment devices disclosed in U.S. patent application Ser. No. 13/715,640, filed Dec. 14, 2012, and published as US 2013-0165953 A1, which is herein incorporated by reference. As shown in FIG. 5, in some embodiments, two suture portions 30A, 30B can be secured together with an exemplary suture clip 34 and also fused together at a connection 32. This can help further secure the sutures together and help prevent the sutures from pulling through the tissue. Any suitable suture clip can be used in such embodiments, such as any of the exemplary suture clips disclosed in U.S. patent application Ser. No. 13/715,640.

Figure 7:
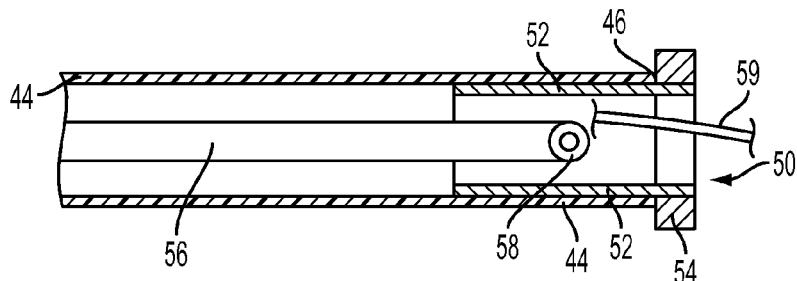
FIG. 7 is a cross-sectional side view of a distal end of the device of FIG. 6.
Figure 8:
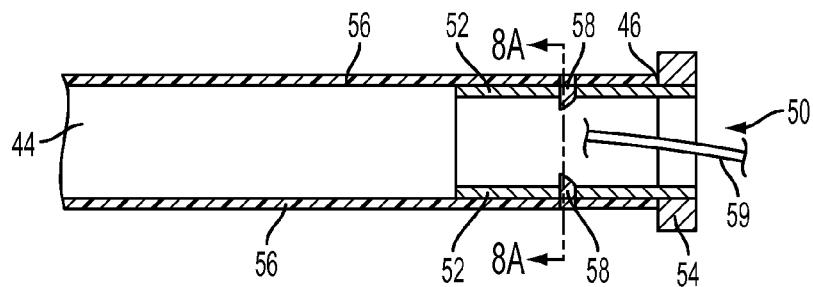
FIG. 8 is a cross-sectional top view of a distal end of the device of FIG. 6.
Figure 8A:
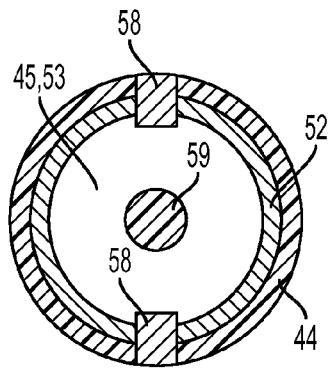
FIG. 8A is a cross-section end view of the distal end of the device of FIG. 6.
Figure 9:
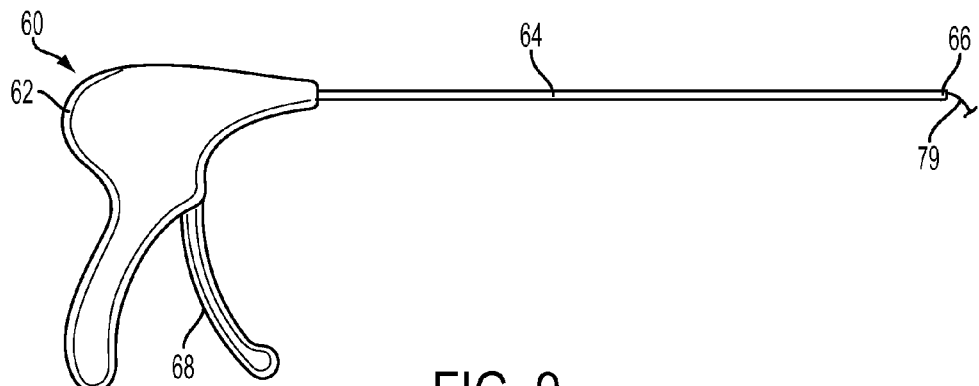
FIG. 9 is a side view of another exemplary suture securement device disclosed herein.

FIGS. 6, 7, 8 and 8A show an exemplary suture clip delivery device 40 that is configured to deploy an exemplary suture clip 50 onto an exemplary suture 59 (the suture 59 shown is not to scale for illustrative purposes, and can be significantly thicker in relation to the clip 50). The device 40 comprises a handle 42 and an elongated shaft 44. The shaft 44 can be long, narrow, and tubular, and can have an inner lumen 45 (FIG. 8A) with a distal opening 46. The clip 50 can be made of an injection molded plastic, machined plastic, other polymeric materials, metal based materials, or other suitable materials. The clip 50 can comprise a support portion 52 having a cross-sectional shape corresponding to the shape of the lumen 45 of the shaft 44, a flanged portion 54 having a broader diameter, and inner passageway 53 (FIG. 8A) extending through the support portion 52 and the flanged portion 54. The broad flange portion 54 can provide increased surface area for contact with tissue to reduce the risk of pull-through or tissue damage. The support portion 52 of the clip can be inserted into the distal opening 46 to load the clip 50 into the device 40. In some embodiments, the support portion 52 and the lumen 45 of the shaft 44 can have a circular cross-sectional profile, as shown in FIG. 8A. In other embodiments, the support portion 52 and the lumen 45 of the shaft can have a non-circular cross-section profile to ensure proper rotational orientation of the clip 50 relative to the shaft. When loaded, the flange portion 54 can abut the distal end of the shaft 44, as shown in FIGS. 7 and 8, which show two cross-sectional views of the distal end of the shaft 44 with the clip 50 loaded, taken along a longitudinal axis of the shaft 44 at 90 degrees apart from each other.

With the clip 50 loaded in the device 40 and a suture 59 inserted into or through the clip, the device can be used to secure the clip to the suture. The device 40 can be configured such that manual actuation of a lever 48, or other mechanism, causes a volume of liquid polymer to be injected through the shaft 44 and into the passageway 53 (FIG. 8A) within the support portion 52 of the clip 50. UV radiation or other curing means can then be used to solidify the polymer inside the clip 50 and thereby secure the clip to the suture via the solid polymer. As shown in FIGS. 7 and 8, the device 40 can further comprise one or more polymer delivery tubes 56 that are coupled at a proximal end to a liquid polymer source, such as in the handle 42 or external to the device 40, and coupled at a distal end to one or more polymer delivery tips 58, which extend radially through the sidewall of the support portion 52 of the clip 50 and into the passageway 53 between the inserted suture 59 and the inner surface of the support portion 52.

The polymeric injection material can comprise, for example, a copolymer resin with a curing agent, a thermopolymer which is heated up and then cools once injected, or other known materials. In some embodiments, once the liquid polymer is injected into the clip, a UV curing device (either part of the device 40 or separate), such as a UV radiation source, can be applied to solidify the polymer. For example, some embodiments of the device 40 comprise a UV radiation source positioned in the handle portion and/or UV radiation emitter positioned near the distal end of the shaft 44. The suture 59 and/or the clip 50 can partially or completely bond with the injected polymer, providing a permanent bond between the suture and the clip.

The cross-sectional size of the shaft 44 and lumen 45 can be any size and can be used with any size of clip 50 and any size of inner passageway 53, which can be used with any size or type of suture 59. The device 40 and clip 50 can also be used to secure more than one suture together in the same manner. In some embodiments, the inner diameter of the passageway 53 through the clip 50 can be sized significantly larger than the diameter of the suture 59, thereby making it easier to insert the suture through the clip and providing space for the polymeric material to be injected.

The support portion 52 of the clip can comprise lateral openings corresponding to the location of the polymer delivery tips 58. In some embodiments, the tips 58 can be rigid to aid in retaining the clip 50 within the shaft 44, and in other embodiment, the tips 58 can be soft and flexible. In some embodiments, the tips 58 can have a curved or sloped distal surface to facilitate inserting the clip support portion 52 over the tips until the tips engage into holes in the sidewall of the support portion, as shown in FIG. 8. The tips 58 can be integrated with the shaft 44 and delivery tubes 56 in some embodiments, and in other embodiments the tips 58 can be integrated with the clip 50 itself. In some embodiment, there is only one polymer delivery tube 56 and/or only one tip 58 for injecting polymeric material into the clip 50, while in other embodiments, there can be more than two delivery tubes 56 and/or more than two tips 58.

In some embodiments, the inner surfaces of the clip 50 can comprise geometric characteristics that prevent the polymeric material from escaping from the clip once solidified.

After the clip 50 is deployed and secured to a suture, the device 40 can be used to cut off the free end of the suture. In some embodiments, the distal end of the shaft 44 can comprise a cutting means, such as a sharp edge, blade, heating element, etc., for cutting the suture.

To aid in releasing the clip 50 from the shaft 44, the device 40 can comprise a release mechanism that causes the clip 50 to separate from the shaft 44, from the delivery tubes 56, and/or from the tips 58. In some embodiments, the clip 50 is held within the shaft 44 via friction fit between the support portion 52 and the inner surface of the shaft 44. In some cases, this friction can be overcome by pulling the device proximally and relying on suture tension to pull the clip in the opposite direction. In some embodiments, a pushing device (not shown) can be positioned within the shaft 44 and proximal to the clip 50, and configured to move distally relative to the shaft 44 in order to push the clip 50 out of the shaft 44 after it is secured to the suture. In some embodiments, the device 40 can be configured to move the tips 58 radially out of the lateral holes in the clip support portion 52 in order to disengage the clip 50 from the device 40.

FIGS. 9, 10, 11, and 11A show another exemplary suture clip delivery device 60 that is configured to deploy an exemplary suture clip 70 onto an exemplary suture 79 (the suture 79 shown is not to scale for illustrative purposes, and can be significantly thicker in relation to the clip 70). The device 60 comprises a handle 62 and an elongated shaft 64. The shaft 64 can be long, narrow, and tubular, and can have an inner lumen 67 with a distal opening 66. A distal end portion of the shaft 64 can comprise a heating element 65, such as an electrical heating element or other means for providing heat.

Figure 10:
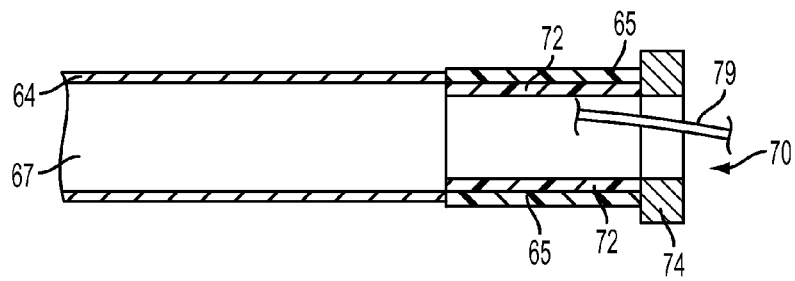
FIG. 10 is a cross-sectional side view of a distal end of the device of FIG. 10.
Figure 11:
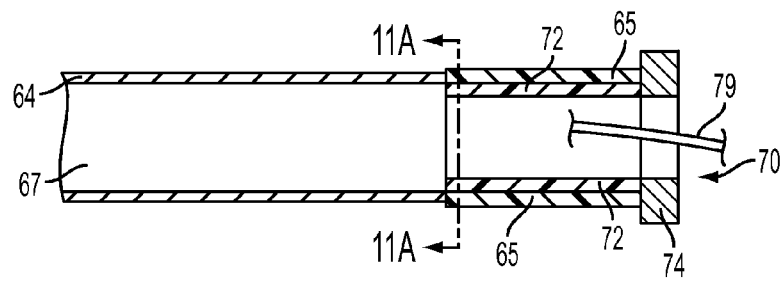
FIG. 11 is a cross-sectional top view of a distal end of the device of FIG. 10.
Figure 11A:
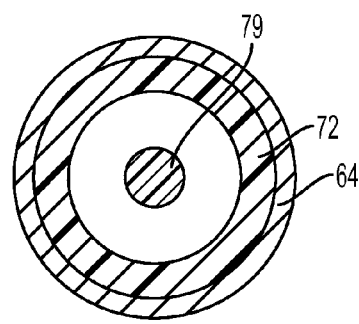
FIG. 11A is a cross-section end view of the distal end of the device of FIG. 10.
Figure 12:
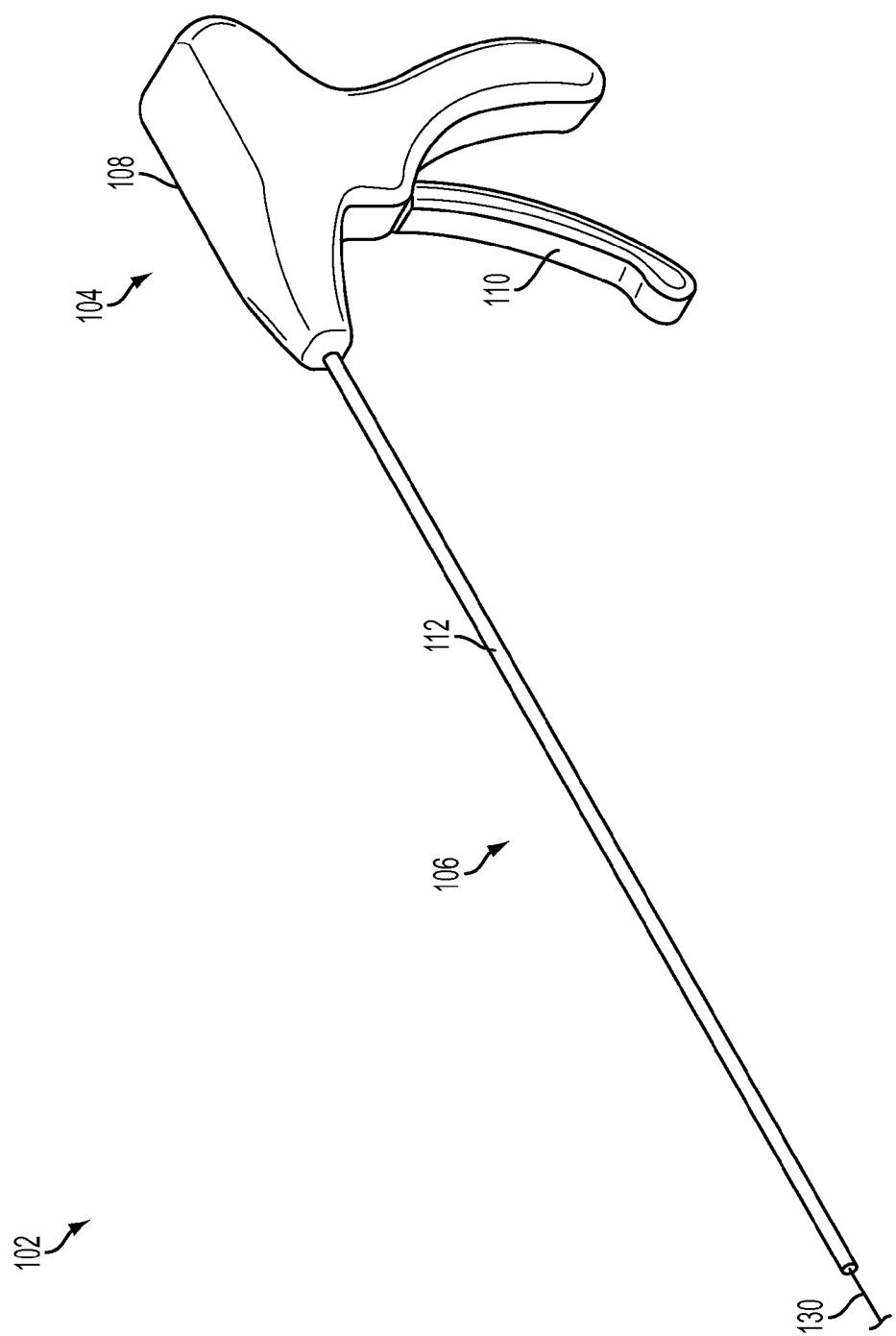
FIG. 12 is a perspective view of another exemplary suture securement device disclosed herein.
Figure 13:
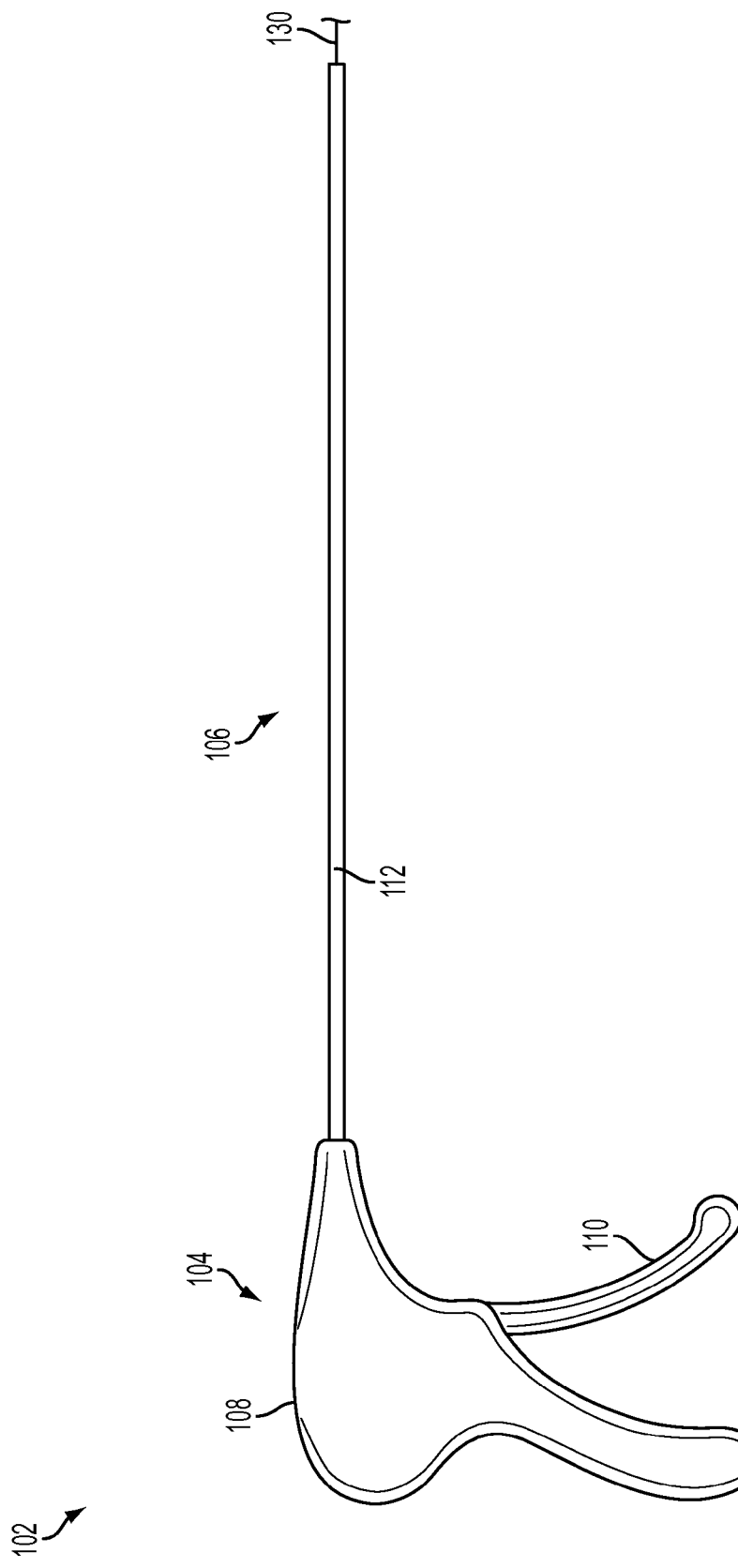
FIG. 13 is a side view of the device of FIG. 12.

The clip 70 can comprises a support portion 72 having a cross-sectional shape corresponding to the shape of the lumen 67 of the shaft 64, a flanged portion 74 having a broader diameter, and inner passageway 73 (FIG. 11A) extending through the support portion and the flanged portion for receiving the suture 79. The broad flange portion 74 can provide increased surface area for contact with tissue to reduce the risk of pull-through or tissue damage. The support portion 72 of the clip can be inserted into the distal opening 66 to load the clip 70 into the device 60. In some embodiments, the support portion 72 and the lumen 67 of the shaft 64 can have a circular cross-section profile. In other embodiments, the support portion 72 and the lumen 67 of the shaft 64 can have a non-circular cross-section profile to ensure proper rotational orientation of the clip relative to the shaft. When loaded, the flange portion 74 can abut the distal end of the shaft 64, as shown in FIGS. 10 and 11, which show two cross-sectional views of the distal end of the shaft 64 with the clip 70 loaded, taken along a longitudinal axis of the shaft 64 at 90 degrees apart from each other.

With the clip 70 loaded in the device 60 and a suture 79 inserted into or through the clip, the device can be used to secure the clip to the suture. The device 60 can be configured such that actuation of a lever 68, or other mechanism, causes the heating element 65 to heat the support portion 72 of the clip. For example, the heating element 65 can be electrically coupled to a battery in the handle 62 and/or to an external power source. Heat from the heating element 65 can cause the support portion 72 to become secured to the suture 79. In some embodiments, the heat can cause the support portion 72 to shrink or constrict radially around the suture 79 to mechanically and/or frictionally secure the clip to the suture. In some embodiments, the heat can cause the support portion 72 and/or the suture 79 to partially melt and bond or adhere together. In some embodiments, the heat can cause the support portion 72 to chemically bond to the suture 79. The support portion 72 of the clip, or the whole clip 70, can comprise a polymeric material, such as thermoset or thermoplastic polymer. In some embodiments, the clip can comprise a single layer polymer, and in some embodiments the clip can comprise a multi-layered polymer. In some embodiments, the clip can comprise a braided material. In some embodiments, the heat can activate an adhesive material coating the inner surface of the support portion 72 such that the adhesive adheres the clip to the suture 79. The suture 79 and the clip 70 can partially or completely bond with each other, providing a permanent, strong bond between the suture and the clip.

In some embodiments, the clip 70 can comprise contoured and/or textured inner surfaces that engages with the suture 79, which can increase contact surface area, increase friction, and can present a tortuous path for suture once the clip has constricted around the suture. This can further enhance the attachment force between the clip and suture and increase retention.

The cross-sectional size of the shaft 64 and lumen 67 can be any size and can be used with any size of clip 70 having any size of inner passageway 73, which can be used with any size or type of suture 79. The device 60 and clip 70 can also be used to secure more than one suture together in the same manner. In some embodiments, the inner diameter of the passageway 73 through the clip 70 can be sized significantly larger that the diameter of the suture 79, thereby making it easier to insert the suture through the clip.

After the clip 70 is deployed and secured to a suture, the device 60 can be used to cut off the free end of the suture. In some embodiments, the distal end of the shaft 64 can comprise a cutting means, such as a sharp edge, blade, heating element, etc., for cutting the suture.

To aid in releasing the clip 70 from the shaft 64, the device 60 can comprise a release mechanism that causes the clip 70 to separate from the shaft 64. In some embodiments, the clip 70 is held within the shaft 64 via a friction fit between the support portion 72 and the inner surface of the shaft. In some embodiments, this friction is reduced or eliminated when the support portion 72 is heated and becomes secured to the suture 79, such as because the support portion shrinks in diameter. In some embodiments, the friction can be overcome by pulling the device 60 proximally and relying on suture tension to pull the clip 70 in the opposite direction. In some embodiments, a pushing device (not shown) can be positioned within the shaft 64 and proximal to the clip 70, and configured to move distally relative to the shaft 64 in order to push the clip 70 out of the shaft after it is secured to the suture.

FIGS. 12-26 show an exemplary embodiment of another suture securement device 102. The device 102 can be used to fuse sutures together and/or cut off free ends of sutures using heat. Sutures can be inserted into a distal end of the device 102 and manually tensioned, then the device can be actuated to apply heat to the sutures to melt them, which can sever off free ends of the sutures and can fuse the sutures together. The device 102 can be applied, for example, to two ends of a single suture that is threaded through a patient's body with the free ends exposed. The two exposed ends of the suture can be inserted into the device 102, tensioned as desired, and then fused together to secure the suture in the body at the desired tension, and the free ends beyond the fused area can be severed and removed, providing an effective suture securement without the use of knots or clips or other retaining devices.

The illustrated embodiment of the device 102 comprises a handle portion 104 and an elongated shaft portion 106 extending from the handle portion. The handle portion 104 can include an outer housing 108 and a trigger 110 for actuating the device. The trigger 110 can comprise a lever that pivots relative to the housing 108, such as about pivot 120 as illustrated in FIG. 14, or can comprise other mechanical or electronic mechanisms for actuating the device, including automated and/or motorized mechanisms.

Figure 14:
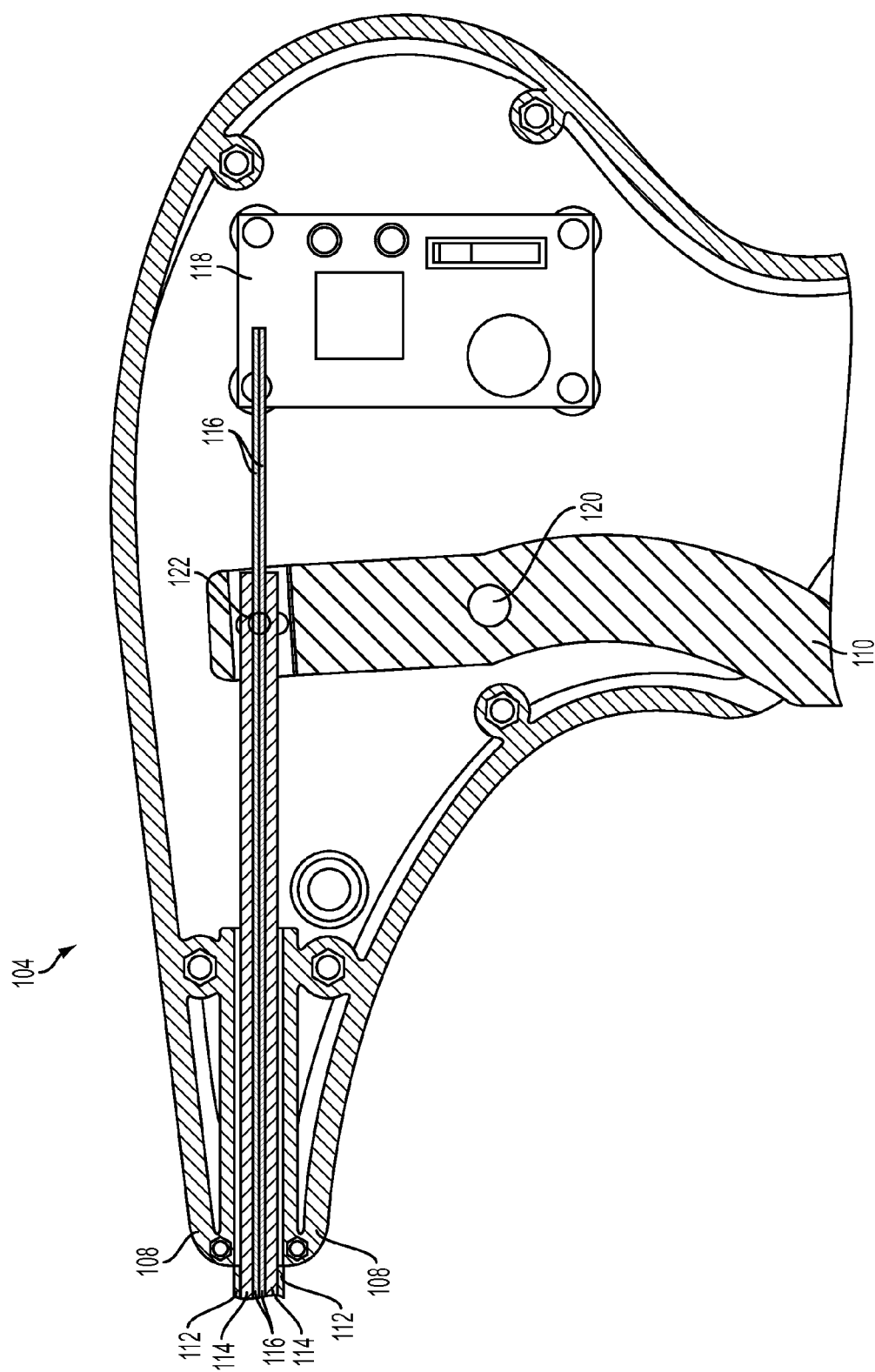
FIG. 14 is cross-sectional side view of a handle portion of the device of FIG. 12.

As shown in FIG. 14, the handle portion 104 can further comprises electronics 118, such as a battery or other power source, within the housing 108 for providing electrical power to a heating element 124 in the shaft portion 106. In other embodiments, the device 102 can be electrically coupled to an external power source for providing electrical power to the heating element 124, such as via a cord that plugs into an outlet.

The shaft portion 106 includes an outer shaft 112 that is fixed to or coupled to the housing 108 and extends distally from the handle portion 104 such that the shaft portion 106 can be inserted into a body cavity to access sutures. An inner shaft 114 is positioned within the outer shaft 112 and is slidably movable proximally and distally within a lumen of the outer shaft 112. A proximal end portion of the inner shaft 114 can be coupled to the trigger 110, such as at pivot 122, in the handle portion 104 such that actuation of the trigger causes the inner shaft to move distally within the outer shaft 112. Releasing the trigger 110 can cause the inner shaft to move back proximally within the outer shaft, such as via a spring or other biasing mechanism (not shown) attached to the inner shaft or the trigger and to the housing 108. In other embodiments, after the trigger 110 is actuated from a starting position to an actuated position, the trigger is manually moved back to the starting position to cause the inner shaft 114 to move back proximally.

Figure 15:
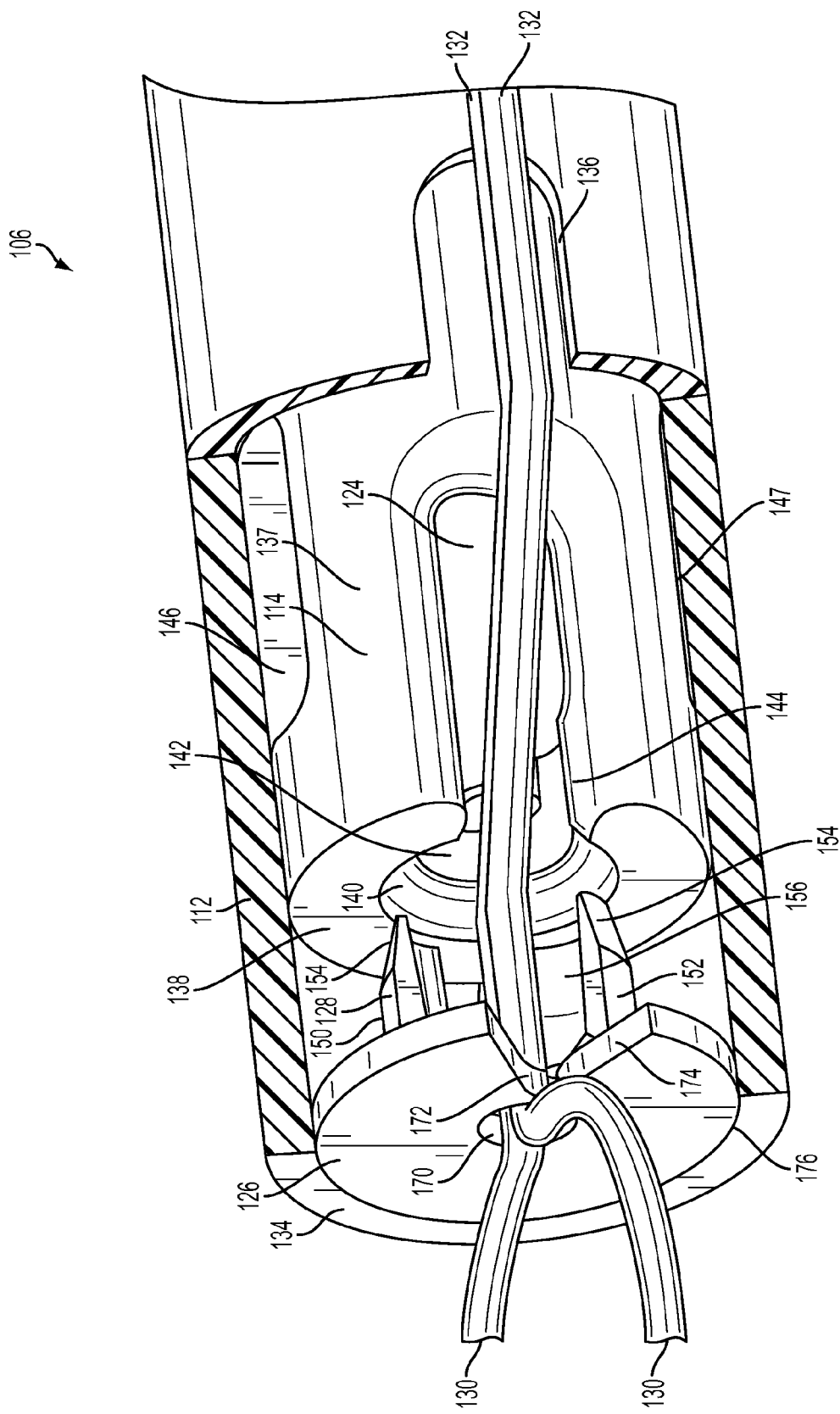
FIG. 15 is a perspective view of a distal portion of the device of FIG. 12 in an open position, with an outer shaft of the device partially cut away.
Figure 16:
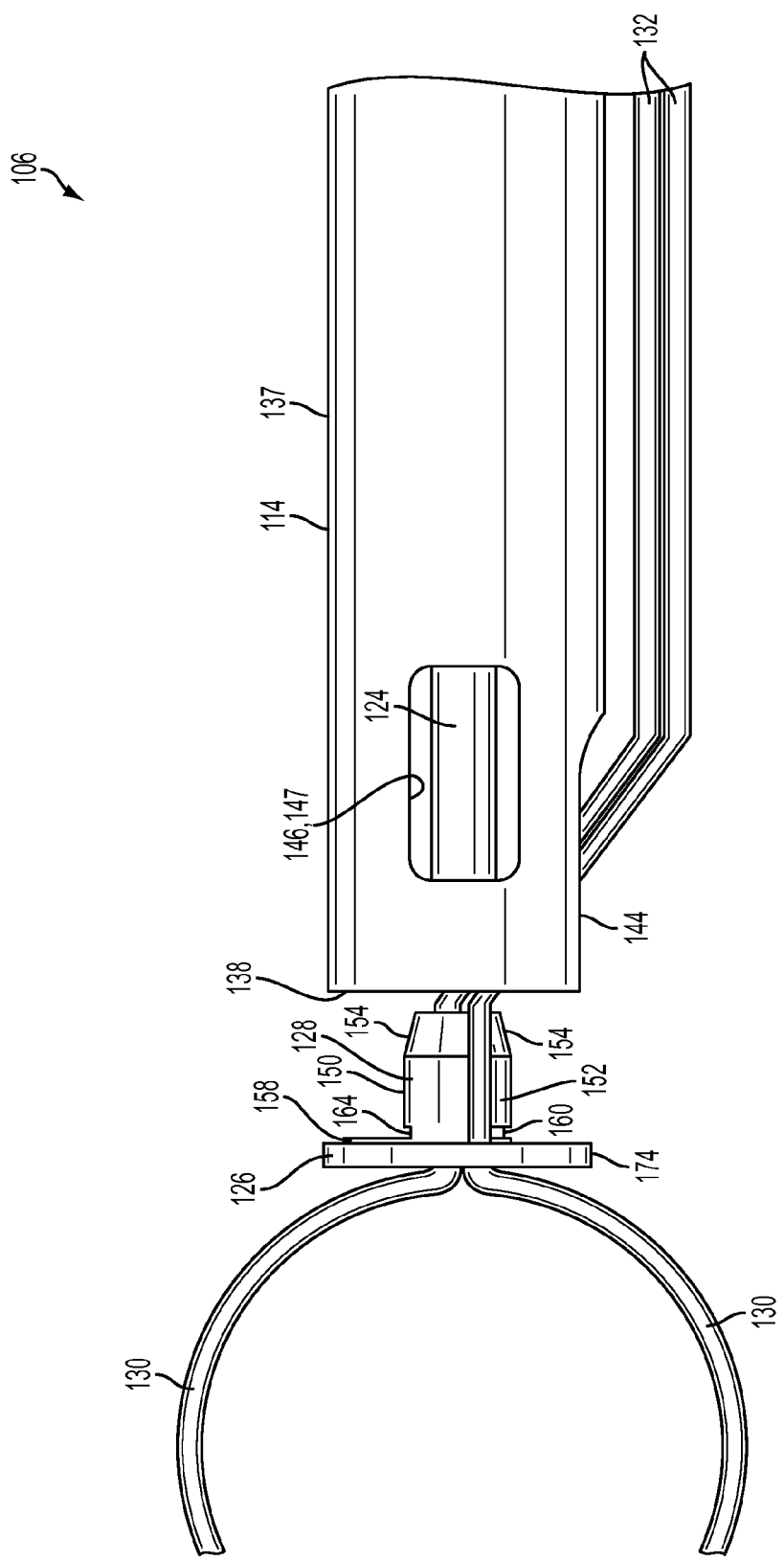
FIG. 16 is a top view of the distal portion of the device of FIG. 12 in the open position, with the outer shaft not shown.

Referring to FIG. 15, the heating element 124 can be positioned within the inner shaft 114 and can move in unison with the inner shaft 114 within the outer shaft 112 in response to actuation of the trigger 110. In FIG. 15, the outer shaft 112 is partially cut away in order to better illustrate other components within the outer shaft. The outer shaft 112 typically extends the entire length of the shaft portion with a distal end positioned around the suture collar 126. The heating element 124 is positioned within the inner shaft 114 and the distal end distal end of the heating element 124 is spaced radially from the inner surfaces 142 of the distal end portion of the inner shaft 114. The heating element 124 can further comprise a proximal portion 125 (FIG. 18) having a larger diameter and mounted further proximally within the inner shaft. The heating element 124 can be coupled to the electronics 118 in the handle portion 104 and/or to an external power source and/or controller via wires 116 running through the shaft portion 106, such as within the inner shaft 114, as illustrated in FIG. 14.

The device 102 has an open configuration, shown in FIGS. 15-18, and a closed configuration, shown in FIGS. 19-22. Actuating the trigger 110 can cause the device 102 to move from the open configuration to the closed configuration, and releasing the trigger 110 or returning the trigger to its pre-actuation position can move the device 102 from the closed configuration to the open configuration.

In the open configuration (FIGS. 15-18), the device 102 can receive sutures 130 at a distal end of the shaft portion 106 and the received sutures can optionally be tensioned by pulling on free ends 132 of the sutures that protrude out of the side of the shaft portion 106. In the closed position (FIGS. 19-22), the received sutures 130 can be gripped by a suture holder 128 to maintain tension in the sutures and/or manual tension can be maintained, and the heating element is applied to the sutures 130 fuse them together and/or cut off the free ends 132 of the sutures.

The outer shaft 112 can be tubular, such as generally cylindrical, or it can have a non-circular cross-section. The shaft 112 defines an inner lumen in which the inner shaft 114 slides. The inner shaft 114 can have an outer surface 137 that generally conforms to the inner lumen of the outer shaft 112 and provides for minimal frictional contact therebetween. As shown in FIG. 15, the distal end portion of the inner shaft 114 can include a distal end 138, a beveled or sloped surface 140, an inner cavity 142 that surrounds the heating element 124, a lateral slot 144 that extends proximally from the distal end 138 in one side of the inner shaft, and/or one or more radial vents 146, 147 communicating from the inner cavity 142 radially to the outer surface 137 proximate the heating element 134.

The outer shaft 112 has a distal end 134, a lateral slot 136 that extends proximally from the distal end 134 in one side of the outer shaft, and/or one or more radial vents (not shown) communicating from its inner lumen radially to its outer surface. The lateral slots 136 and 144 can be aligned circumferentially to provide a lateral opening extending radially through both the inner and outer shafts. Vents in the outer shaft 112 can further be aligned, both circumferentially and longitudinally, with the vents 146, 147 in the inner shaft 114 when the inner shaft is in the distal, closed position in order to vent heat from the heating element radially out of the device and/or to allow cross-flow of air through the shaft portion 106 past the heating element.

In some embodiments, the device 102 can further comprise a suture collar 126 at the distal end 134 of the outer shaft 112. The collar 126 can be generally disk shaped having generally flat distal and proximal surfaces and a round perimeter 176 that mounts within the distal end of the inner lumen of the outer shaft. The collar 126 includes a central opening 170 that can receive and collar sutures extending proximally through the collar 126 into the inner lumen of the outer shaft. The collar 126 can further comprise a lateral gate 172 to allow intermediate portions of sutures to be inserted laterally into the central opening 170 but restricts or prevents sutures from escaping laterally out of the central opening.

Figure 26:
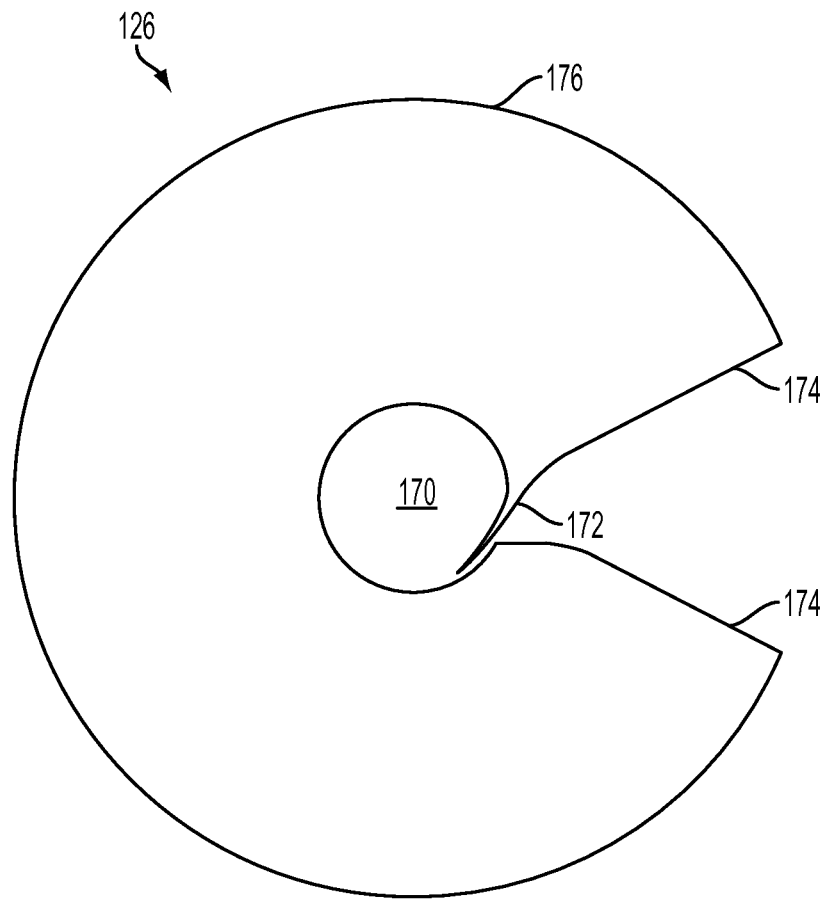
FIG. 26 is distal end view of an exemplary suture collar of the device of FIG. 12.

As shown in FIG. 26, the collar 126 includes a radial slot or mouth 174 that extends from the lateral gate radially to the outer perimeter 176. The radial slot 174 can be generally tapered or wedge shaped, such that its width decreases moving radially inwardly. This can assist in directing an intermediate portion of a suture radially toward the lateral gate 172 and into the central opening 170. The radial slot 174 can be circumferentially aligned with the lateral slots 136, 144 in the outer and inner shafts 112, 114, to allow sutures to be inserted laterally into the collar 126 and into the suture holder 128 with free ends of the sutures extending laterally out through the lateral slots in the shafts.

As shown in FIG. 26, the lateral gate 172 can comprise a tang or flap that extends generally circumferentially along the side of the central opening 170, blocking communication between the radial slot 174 and the central opening 170. The lateral gate 172 can be elastically deformable such that radially inward force from a suture being moved radially inwardly through the radial slot 174 causes the lateral gate 172 to resiliently deflect into the central opening 170, opening a passageway between radial slot and the central opening large enough for the suture to pass through into the central opening. The lateral gate 172 can extend past the radial slot 174 and overlap the radial surface surrounding the central opening such that the lateral gate is blocked from deflecting radially outwardly, which can prevent collared sutures from moving radially outwardly from the central opening 170 through the radial slot 174 and escaping from the collar 126.

In embodiments of the device 102 comprising a suture holder 128, the suture holder 128 can be positioned within the distal end portion of the outer shaft, such as mounted to a proximal surface of the suture collar 126 and/or mounted to an inner surface of the outer shaft 112. The suture holder 128 has an open position (FIGS. 15-18) and a closed position (FIGS. 19-25). In the open position, the suture holder 128 is configured to receive sutures axially and/or radially entering the suture holder, and in the closed position the suture holder is configured to grip and hold received sutures and prevent longitudinal and radial movement of held sutures relative to the outer shaft 112. The suture holder 128 is shown isolated in the closed position in FIGS. 23-25.

The suture holder 128 can comprise a first portion 152 and a second portion 150 that are hingedly coupled together for articulation between the open position and the closed position, such as in a clamshell-type configuration. The first portion 152 of the suture holder can be fixed to the suture collar and/or to the outer shaft, while the second portion 150 is free to move between the open and closed positions.

Figure 19:
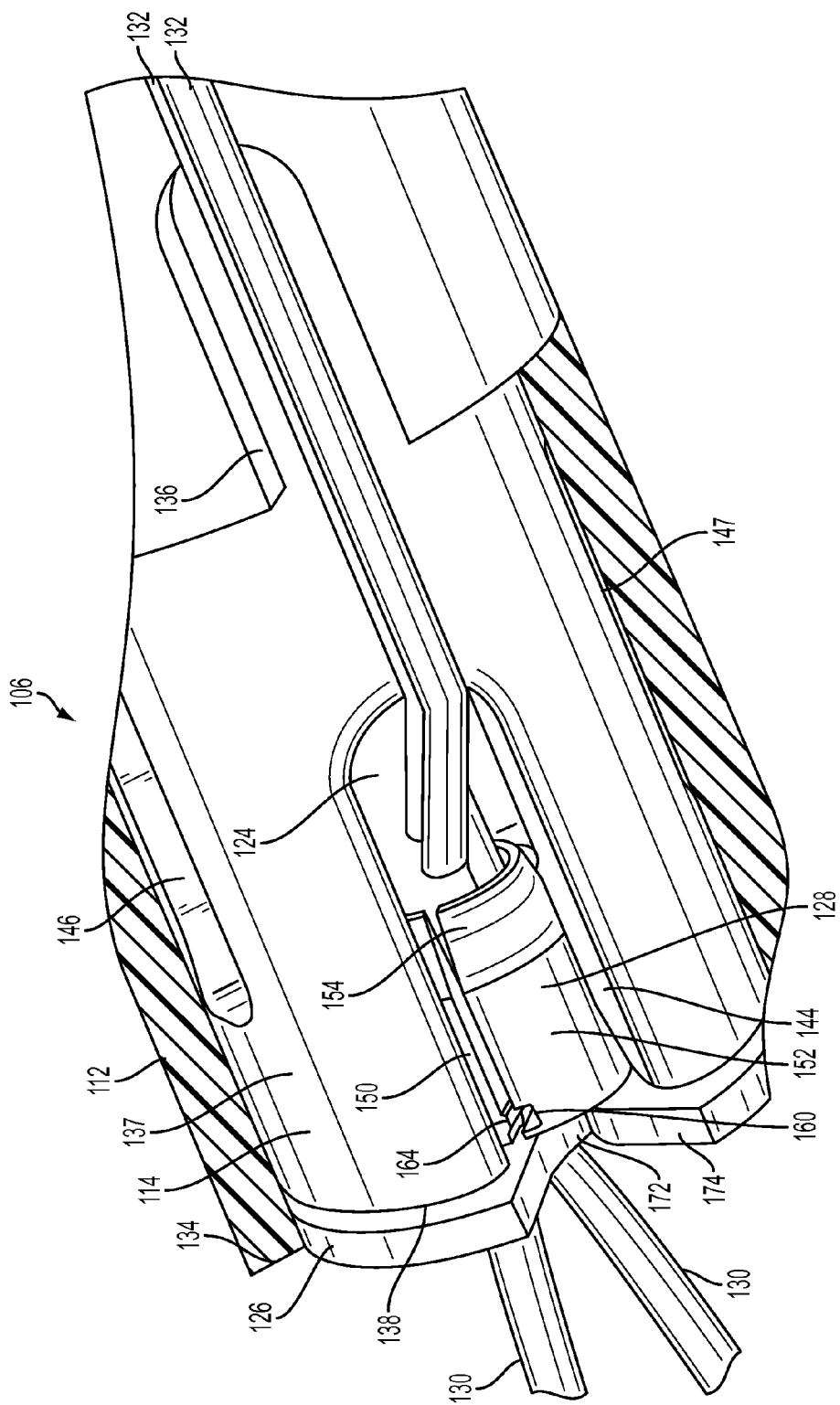
FIG. 19 is a perspective view of a distal portion of the device of FIG. 12 in closed position, with an outer shaft of the device partially cut away.
Figure 20:
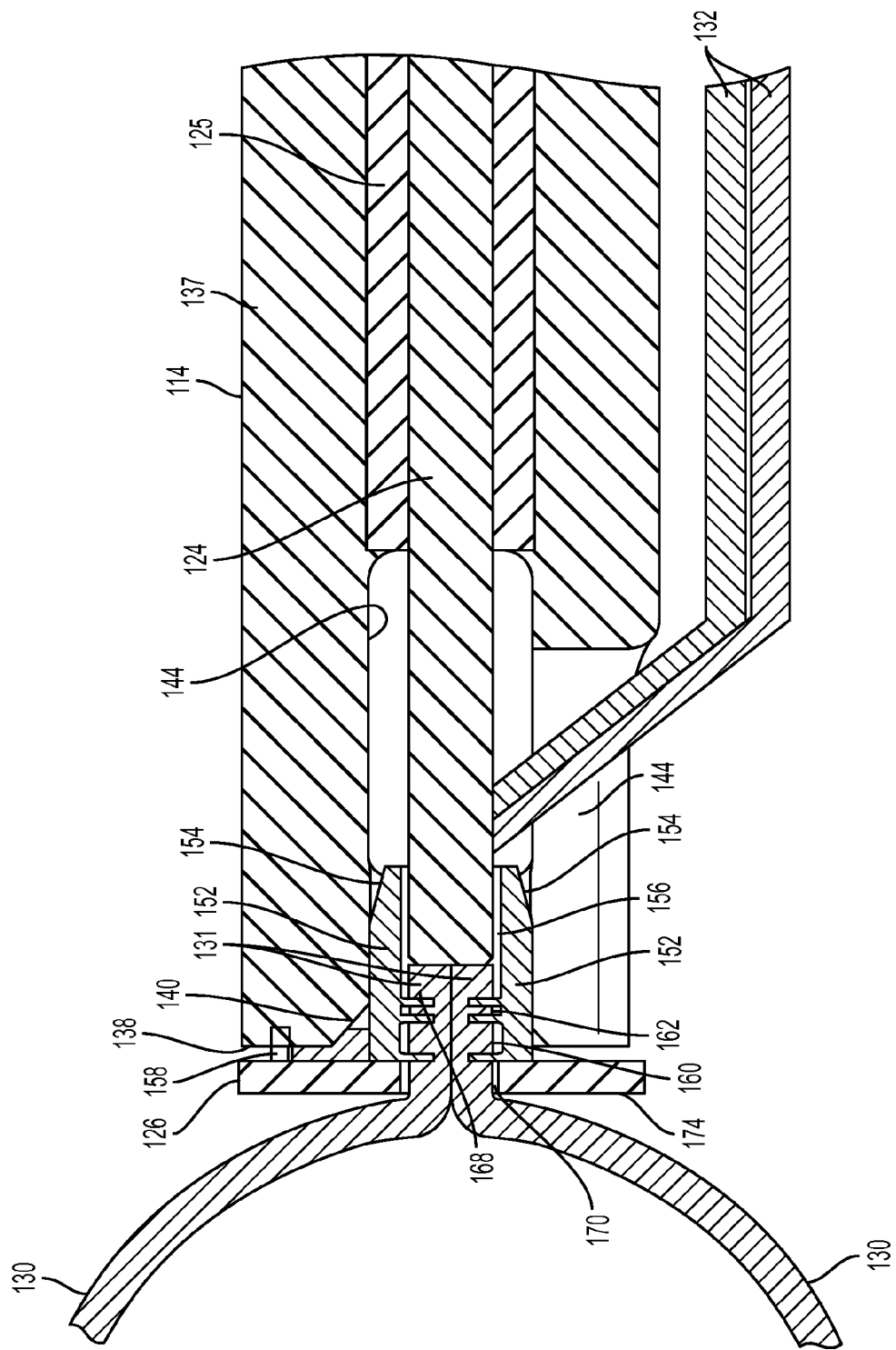
FIG. 20 is a cross-sectional top view of the distal portion of the device of FIG. 12 in a closed position, with the outer shaft not shown.
Figure 21:
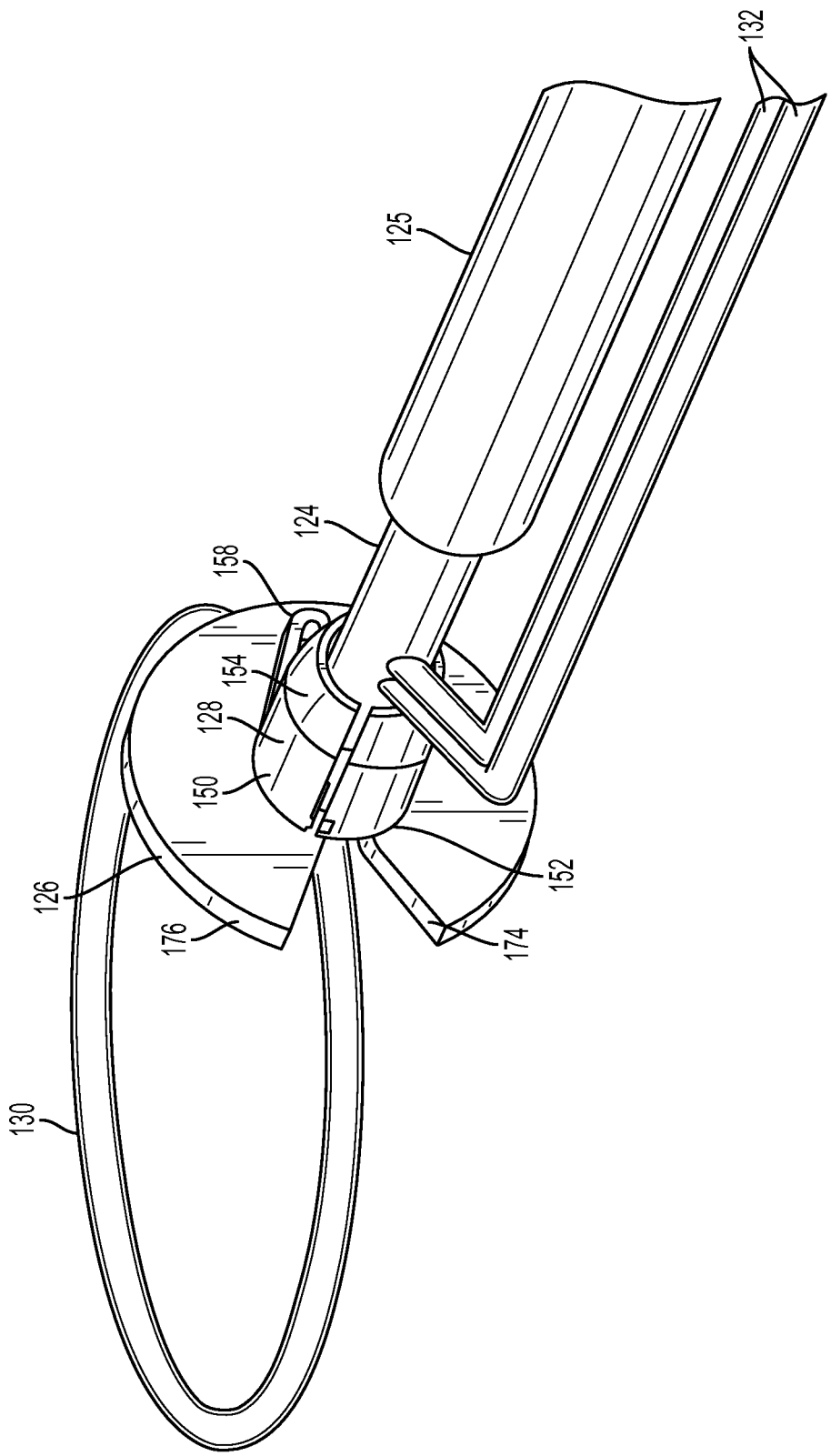
FIG. 21 is a perspective view of the distal portion of the device of FIG. 12 in the closed position, with the outer shaft and inner shaft not shown.

The suture holder 128 can comprise a sloped or tapered proximal outer surface 154 extending circumferentially around, or partially around, both the first and second portions of the suture holder. In other embodiments, the sloped surface 154 may be present only on the movable second portion 152. As the inner shaft 114 moves distally during actuation of the device 102, the sloped surface 140 at the distal end of the inner shaft (see FIG. 15) can contact the sloped surface 154 at the proximal end of the suture holder, and the engagement of these sloped surfaces causes the movable second portion 150 of the suture holder to move toward the first portion 152 and close the suture holder to the closed position. In the closed position, as shown in FIGS. 19 and 20, the inner surface 142 of the inner shaft 114 overlies outer surfaces of the suture holder 128 and retains it in the closed position. In FIG. 19, the outer shaft 112 is partially cut away in order to better illustrate other components within the outer shaft.

As best shown in FIGS. 23-25, the suture holder 128 can include a biasing mechanism 158, such a resiliently flexible connector or spring member, that couples the first and second portions of the suture holder together, allows for controlled motion between the open and closed positions, and biases the suture holder toward the open position. Due to the opening bias, when the inner shaft 114 is retracted proximally and it moves out of restraining contact with the outer surfaces of the suture holder, the suture holder can resiliently move back to the open position, releasing the fused together sutures held in the suture holder.

Figure 17:
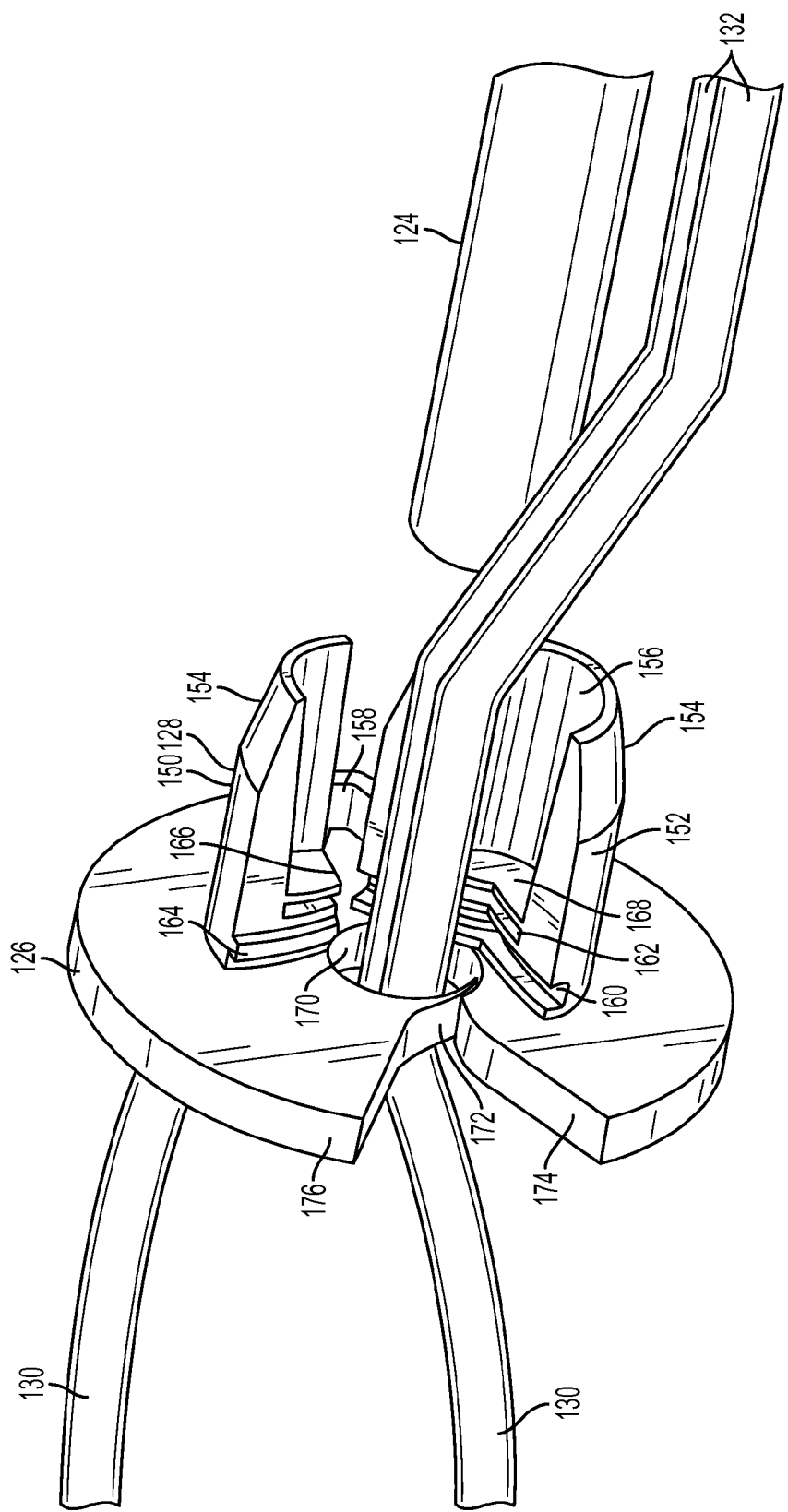
FIG. 17 is a perspective view of the distal portion of the device of FIG. 12 in the open position, with the outer shaft and inner shaft not shown.
Figure 18:
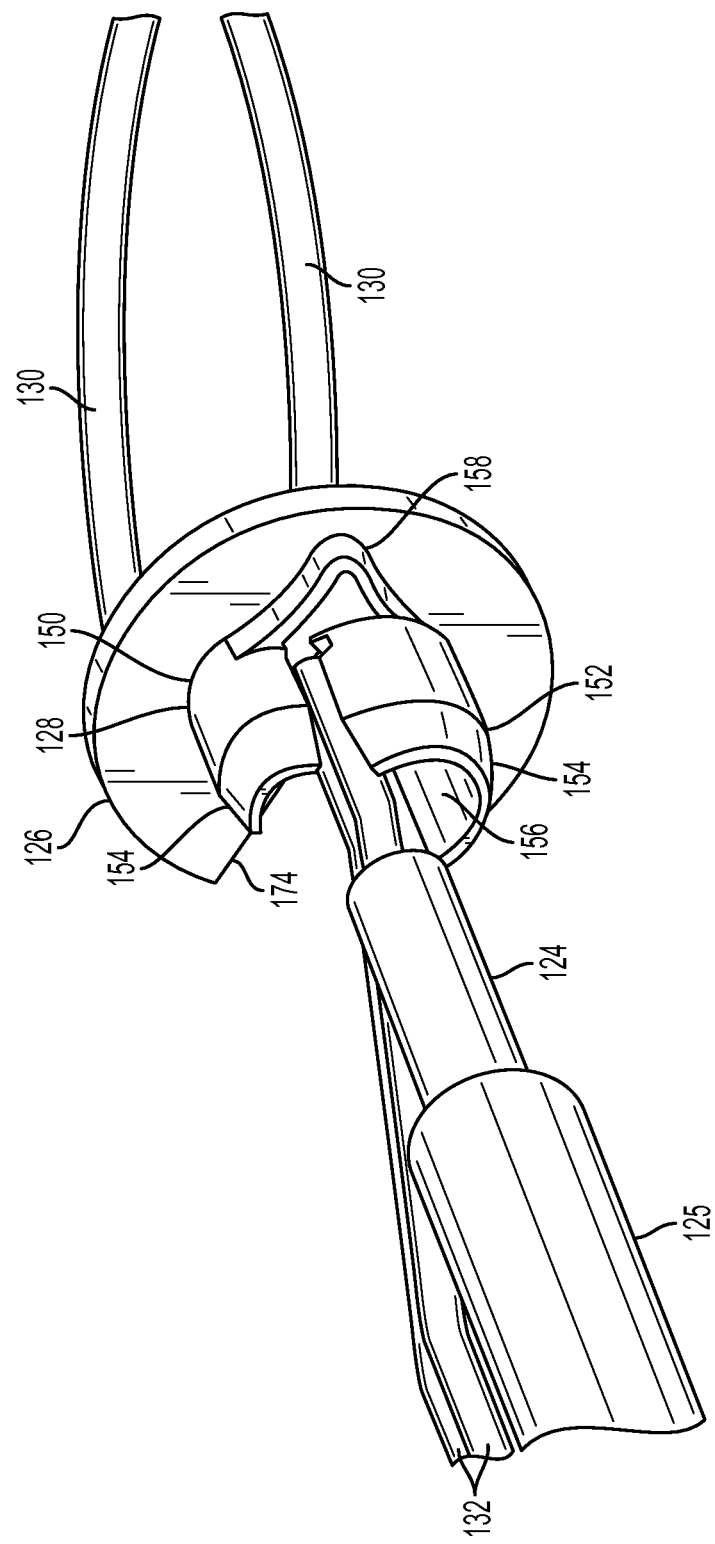
FIG. 18 is another perspective view of the distal portion of the device of FIG. 12 in the open position, with the outer shaft and inner shaft not shown.

As best shown in FIG. 17, the suture holder 128 can include one or more grooves or recesses (e.g. 160, 162) and/or one or more ridges or projections (e.g., 164, 166) on opposing surfaces of the first and second portions 150, 152 of the suture holder to enhance its ability to securely grip received sutures and keep them from moving longitudinally relative to the suture holder in the closed position. For example, the ridge 164 can cooperate with the groove 160 to pinch or kink held sutures, and the ridge 166 can cooperate with the groove 162 to pinch or kink held sutures. In some embodiments, other forms of traction enhancement can be provided, such as surface texturing or teeth, to help grip the sutures.

The suture holder 128 can further comprises a proximal recess or cup 156 formed between the first and second portions 150, 152 of the suture holder when in the closed position (FIG. 22). The distal floor of this cup 156 can be formed, for example, by walls of the ridge 166 and the groove 168. The cup 156 can be generally cylindrical in shape, or can taper is diameter moving distally, or can have other shapes. In the closed position, held sutures 130 pass through the cup 156 proximally before bending radially outwardly and exiting through the lateral slots 144, 136 in the inner and outer shafts.

The cup 156 of the suture holder 128 can receive a distal end of the heating element 124, which can have a diameter slightly smaller than the inner diameter of the cup, when the device 102 is actuated and the heating element moves distally within the outer shaft 112. As the heating element moves into proximity with the cup 156, the heating element can contact the held sutures 130 and begin to melt them. As the heating element 124 enters the cup 156, the free ends 132 of the suture can be severed off. Within the cup 156, the remaining ends of the held sutures 130 can be melted and fused together, forming a fused region that conforms generally to the shape of the cup and the distal end of the heating element 124. When the heating element is subsequently retracted proximally from the cup 156, the fused portion of the sutures 130 can cool and harden, forming a secure connection between the sutures. Any number of sutures can be cut and/or fused at the same time in this manner, though typically two sutures are acted upon at a time. The fused portion of the sutures can be small enough such that, when the suture holder 128 opens, the fused portion of the sutures can slide distally out of the device 102 through the central opening 170 of the suture collar 126. In some embodiments, surfaces of the suture holder 128 can be coated with a non-stick material, such as PTFE, to help release the fused sutures.

An exemplary method of using the device 102 can comprise the following. One or more sutures can initially be placed in a subject, be it a human patient or animal. The placed suture or sutures can have free portions extending from the subject that require securement at a desired tension. Instead of tying the free portions in knots or applying bulky clips to secure the sutures, the device 102 can be used to fuse the sutures together to secure them and/or cut off the remaining free portions.

Intermediate portions of the tensioned sutures (i.e., portions of the sutures spaced from ends of the sutures) can be laterally inserted into the distal end portion of the shaft portion 106 of the device 102. To do this, the distal end of the shaft portion 106 of the device can be placed adjacent to the location where a suture exits the tissue or other structure of the subject. While the suture is manually held under tension, an intermediate portion of the suture can be forced to move laterally into the radial slot 172 of the suture collar 128 and into the lateral slot 136 of the outer shaft 112. This can be done by urging the shaft portion 112 (in the open position) against the side of a tensed suture, for example. As the suture moves radially inwardly through the radial slot 172, it can contact the lateral gate 172, causing it to open inwardly, and allowing the suture to move into the central opening 170 of the suture collar 126. The suture also moves laterally into the open suture holder between the first and second portions 150, 152.

Once the sutures have been collared within the central opening 170 of the suture collar 126, the tension on the sutures can be manually adjusted to a desired level by pulling the ends 132 of the sutures and/or by pressing the distal end of the shaft portion 106 against the tissue or structure from which the sutures project. Once the sutures are collared and under the desired tension, the device 102 can be actuated.

Pulling the trigger 110, or otherwise causing actuation of the device 102, causes the inner shaft 114 and heating element 124 to move distally relative to the outer shaft 112, suture collar 126, and suture holder 128. Distal motion of the inner shaft 114 causes contact between the slope surface 140 of the inner shaft and the sloped surface 154 of the suture holder 128, which closes the suture holder and grips the sutures at the desired tension. For example, actuation of the device 102 can be done while the distal end of the shaft portion 106 is pressed against tissue around the suture exit point to maintain the desired tension. Actuation of the device 102 also causes the heating element 124 to heat up and move into contact with the sutures proximal to the gripping location of the sutures. The heating element 124 can be fully heated to an operative temperature before it contacts the sutures, or can be partially heated at contact with the sutures, in order to provide desired cutting and fusing properties. Once in contact with the sutures, the heating element 124 can be maintained in contact with the sutures at the operative temperature for a period of time, such as up to 5 seconds, such as 2 to 3 seconds, to fully fuse and/or sever the sutures.

The heating element 124 then be retracted or allowed to remain in contact with the sutures in the closed/actuated position for an additional period of time, such as up to another 10 seconds, such as 4-5 seconds, to allow the heating element to cool down and allow the fused portion of the sutures to cool and harden while the distal end of the heating element remains inserted into the cup 156 to provide a mold wall that helps shape and contain the cooling fused portion until it is fully solid. The electronics 118 in the handle portion 104 can control the time period before the current to the heating element is reduced or turned off to allow it to cool down. For example, the electronics 118 can apply power to the heating element for a predetermined period of time after the trigger 110 is fully actuated. In other embodiments, temperature sensors can be located at or near the heating element and/or the suture holder and can sense the temperature of the heating element and/or the fused portion of the sutures and can feed such temperature data back to the electronics such that the electronics can determine when to provide and/or cut the power to the heating element based on the sensed temperature date. In other embodiments, sensed temperature data can be displayed at the handle or elsewhere to allow a user to decide, based on the displayed temperature data, when to release the trigger 110, or otherwise de-actuate the device, and separate the heating element from the fused sutures. The vents 146, 147 in the inner shaft, vents in the outer shaft, and lateral slots 136, 134 in the shafts can provide enhanced cooling of the heating element by allowing airflow and convection cooling, such that the cooling time needed can be reduced, and desirably shortening the entire process.

When the device is de-actuated, the heating element 124 and inner shaft return distally within the outer shaft and the suture holder 128 can resiliently open, releasing the fused sutures to slide out of the device through the central opening 170 of the collar 126.

The device 102 can be reusable any number of time to subsequently secure and/or cut additional sutures. After releasing one fused group of sutures, the device can be immediately ready to be reused on other sutures. Further, in many embodiments, no clips or other devices or materials are consumed by the device or need to be loaded into the device prior to use. However, in other embodiments, the device 102 can be configured to be used to deploy a suture clip or to sutures, such as described with the embodiments of FIGS. 6-11.

Figure 27:
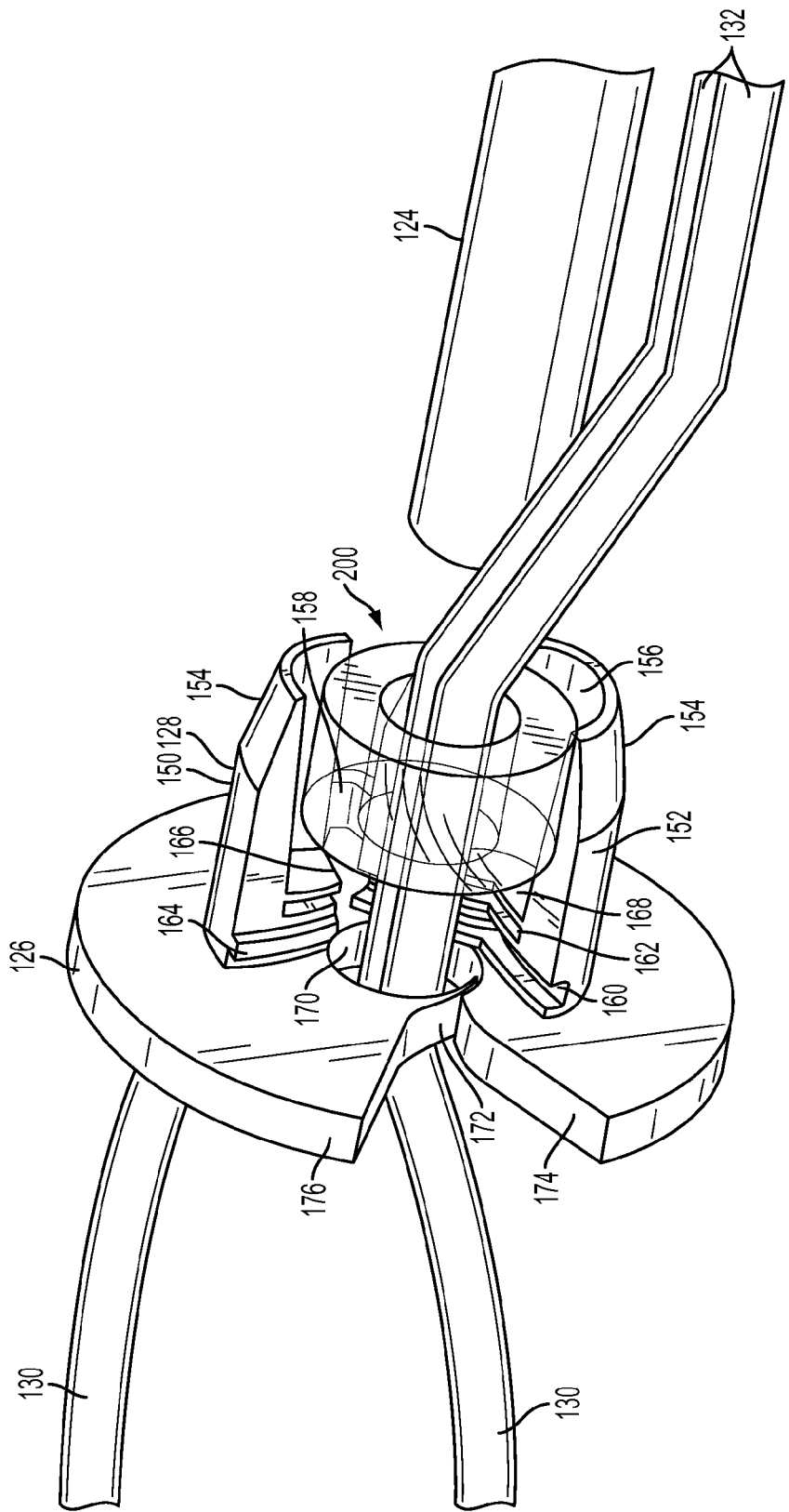
FIG. 27 is a perspective view of the distal portion of the device of FIG. 12 in the open position, with the outer shaft and inner shaft not shown, and further comprising an exemplary fusing sleeve positioned around the sutures.

In still other embodiments and methods, the device 102 can be used with a fusing sleeve to help fusing the sutures together. For example, FIG. 27 shows the device 102 with an exemplary fusing sleeve 200 positioned around the sutures 130 within the suture holder 128, such as in the cup portion 156 of the suture holder. The suture holder 128 may be slightly larger in such embodiments to accommodate the fusing sleeve 200. When the device 102 is actuated, the heating element 124 can melt and/or shrink the sleeve 200 to help secure the sutures together. In some cases, the sutures and the sleeve 200 can melt and fuse together to form a single fuse. In some cases, the sutures may comprise a material that does not naturally fuse together well, and the sleeve 200 can provide or strengthen the bond between the sutures. In some cases, the sleeve 200 may shrink circumferentially instead of or in addition to melting, thereby constricting around the sutures to hold them together. The sleeve 200 can comprise a polymeric material, such as a thermoplastic or thermoset. For example, the sleeve 200 can comprise LDPE, HDPE, PEBAX, PU, and/or other polymers. In other embodiments, the sleeve 200 can comprise materials other than polymers that can melt, shrink, and/or fuse together to the sutures to strengthen the attachment between the sutures. The sleeve 200 can be positioned around the sutures prior to inserting the sutures into the suture holder. With the sleeve 200 positioned around the sutures, the sleeve can be inserted laterally through the slot in the outer shaft and into the cup portion 156 of the suture holder along with the sutures, and then the device can be actuated.

In some embodiments, the device 102 can further comprise an active cooling system to speed up the cooling process after the heating element has fused the sutures together. Such an active cooling system can be included as an alternative to, or in addition to, a passive cooling systems, such as the radial vents 146, 147. In some embodiments, an active cooling system can comprise an air conduit extending along the shaft portion, such as along the outer shaft, from the handle portion to adjacent the suture holder. The air conduit can be coupled to a pressurized air source that blows air over the suture holder, the heating element, and/or the fused sutures to speed up the cooling process. For example, the air source can be an external air supply source in an operating room or can be a pump in the handle portion of the device.

Some embodiments of devices disclosed herein can be used to fuse sutures extending from opposite directions through the device, rather than sutures that extend in the same direction as is shown in FIG. 4. For example, one or more sutures can extend from a first exit point in the tissue or a prosthetic device, into the device through a lateral slot in the outer shaft, through the suture holder, through the suture collar, and have its free end or ends extending out from the suture collar. One or more other sutures can extend from a second exit point in the tissue or the prosthetic device, into the device through the suture collar, through the suture holder, and have free end or ends extending out through the lateral slot in the outer shaft, such that the sutures lay generally parallel through the device but extend in opposite directions from the different exit points. In such an arrangement, the oppositely extending sutures can be fused together with the device with their free ends projecting in opposite directions. This can result in the fused sutures being able to lay flat against a surface of the tissue or a surface of the prosthetic device between the exit points of the opposing sutures. This can also reduce the risk of the fused connection failing when tension is applied to the fuse due the two sutures being pulled in opposite directions.

Any suitable materials can be used in the construction of the device 102. For example, the housing, trigger, inner and outer shafts, heating element, suture holder, and/or suture collar can all comprise stainless steel and/or other suitable materials. The components of the device 102 are desirable sufficiently rigid to be structurally supportive, have sufficient resilient deformability, such as in the case of the lateral gate of the suture collar and suture holder biasing member, have sufficient resistance to heat released by the heating element, do not bond with the suture material, are non-toxic and otherwise not physiologically harmful, can be sterilized, and/or have other desirable properties.

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the term "and/or" used in a list of elements means any one or more of the listed elements. For example, the phrase "A, B, and/or C" means "A," "B," "C," "A and B," "A and C," "B and C" or "A, B and C."

As used herein, the term "coupled" generally means physically or electrically linked and does not exclude the presence of intermediate elements between the coupled items absent specific contrary language.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims. We therefore claim all that comes within the scope of these claims.

We claim:

1. A suture securement device, comprising:
a handle;
an elongated outer shaft having a proximal end portion coupled to the handle and a distal end portion opposite the proximal end;
an inner shaft movable proximally and distally within the outer shaft;
a suture holder at the distal end portion of the outer shaft, the suture holder having an open position and a closed position, wherein in the open position the suture holder is configured to receive sutures, and in the closed position the suture holder is configured to hold sutures and prevent longitudinal movement of held sutures relative to the outer shaft; and
an electrical heating element positioned within the outer shaft;
wherein actuation of the device causes the inner shaft and the heating element to move distally relative to the outer shaft and the suture holder, such that the distal end portion of the inner shaft causes the suture holder to move from the open position to the closed position, and such that the heating element moves into the proximity of the suture holder to fuse together sutures held by the suture holder;
wherein the suture holder is adapted to separate from the fused sutures after the sutures are fused together and the suture holder is adapted to remain part of the suture securement device as the suture securement device is withdrawn from the fused sutures.

2. The device of claim 1, wherein the suture holder comprises a first portion and a second portion that are hingedly coupled together for articulation between the open position and the closed position.

3. The device of claim 2, wherein the first and second portions of the suture holder are coupled by an elastically flexible hinge that biases the first and second portions toward the open position, such that the suture holder releases the fused sutures when the inner shaft moves proximally off of the suture holder.

4. The device of claim 2, wherein the first and second portions of the suture holder are both configured to move relative to the outer shaft when the suture holder articulates between the open and closed positions.

5. The device of claim 1, wherein a first portion of the suture holder is fixed relative to the outer shaft and a second portion of the suture holder moves between the open position and the closed position.

6. The device of claim 5, wherein the first portion of the suture holder is fixed to a proximal side of a suture collar at the distal end of the outer shaft.

7. The device of claim 6, wherein the suture collar comprises a central opening for collaring sutures received by the suture holder, and a lateral gate that allows sutures to enter laterally into the central opening in a radially inward direction through the lateral gate, and the lateral gate blocks sutures from exiting the central opening in a radially outward direction.

8. The device of claim 7, wherein the outer shaft comprises a slot extending proximally from a distal end of the outer shaft, the slot being circumferentially aligned with the lateral gate in the suture collar and a lateral opening in the suture holder such that an intermediate portion of a suture can be laterally inserted through the slot and through the lateral gate and into the central opening and into the suture holder.

9. The device of claim 1, wherein the suture holder has a sloped proximal surface and the inner shaft has a sloped distal surface, and contact between the sloped proximal surface and the sloped distal surface upon distal movement of the inner shaft causes the suture holder to close.

10. The device of claim 1, wherein the suture holder comprises a proximal recess and the heating element is moveable at least partially into the proximal recess.

11. The device of claim 1, wherein the heating element is configured to cut off free ends of the sutures held by the suture holder as the heating elements moves into the proximity of the suture holder.

12. The device of claim 1, wherein the inner shaft comprises a longitudinal slot at the distal end portion of the inner shaft and, in the closed position, free ends of sutures held by the suture holder extend out of the device through the longitudinal slot.

13. The device of claim 1, wherein the outer shaft comprises a longitudinal slot at the distal end portion of the outer shaft and, in the open position, free ends of sutures received by the suture holder extend out of the device through the longitudinal slot to allow manual tensioning of the sutures.

14. The device of claim 1, wherein the heating element is positioned within the inner shaft and the inner shaft comprises at least two radial openings adjacent to the heating element to vent heat from the heating element.

15. The device of claim 1, wherein the suture holder is configured to receive the sutures with a heat-activated sleeve positioned around the sutures, such that the sleeve is received within the suture holder and the sleeve fuses to the sutures in response to heat from the heating element.

16. The device of claim 1, further comprising an air conduit extending from the handle to the distal end portion of the outer shaft and configured to conduct air to the distal end portion of the outer shaft to help cool the heating element or fused sutures.

17. The device of claim 1, wherein the device is configured to receive sutures to be fused such that the sutures extend axially through a distal opening in the device and axially through the suture holder.

18. A suture securement device, comprising:
a handle;
an elongated outer shaft having a proximal end portion coupled to the handle and a distal end portion opposite the proximal end;
a suture collar at the distal end portion of the outer shaft, the suture collar having a central opening for collaring sutures and a lateral gate that allows an intermediate portion of a suture to enter laterally into the central opening in a radially inward direction through the lateral gate, and the gate blocks sutures from exiting the central opening in a radially outward direction; and
an electrical heating element positioned within the outer shaft;
wherein actuation of the device causes the heating element to fuse together sutures collared by the suture collar;
wherein the outer shaft comprises a slot extending proximally from a distal end of the outer shaft, the slot being circumferentially aligned with the lateral gate in the suture collar such that intermediate portions of a sutures can be laterally inserted through the slot in the outer shaft and through the lateral gate and into the central opening to collar the sutures.

19. The device of claim 18, wherein the suture collar is generally disk-shaped and further comprises a generally wedge-shaped slot extending radially from a radially outer perimeter of the suture collar to the lateral gate.

20. The device of claim 18, wherein the lateral gate comprises an elastically flexible flap that deflects to allow sutures to pass into the central opening.

21. The device of claim 20, wherein radially inward force from a suture causes the flap to elastically deflect into the central opening to open the lateral gate.

22. A suture securement device, comprising:
a handle portion comprising a trigger and an electrical power source; and
an elongated shaft portion extending from the handle portion, the shaft portion comprising:
a tubular outer shaft having a proximal end attached to the handle portion, a distal end opposite the proximal end, an inner lumen, and an outer slot extending proximally from the distal end of the outer shaft;
an inner shaft having a proximal end coupled to the trigger, a distal end opposite the proximal end, an inner slot extending proximally from the distal end of the inner shaft, the inner shaft being movable longitudinally within the inner lumen of the outer shaft via actuation of the trigger;
a suture collar at the distal end of the outer shaft, the suture collar having a central opening for collaring sutures and a lateral gate that allows sutures to laterally enter into the central opening in a radially inward direction via the outer slot in the outer shaft, and the gate blocks sutures from exiting the central opening in a radially outward direction;
a suture holder comprising a first portion and a second portion that are hingedly coupled together, the first portion being attached to a proximal side of the suture collar and the second portion being free to articulate between an open position and a closed position, wherein in the open position the suture holder is configured to receive sutures between the first and second portions that extend through the central opening of the suture collar, and in the closed position the first and second portions of the suture holder close together to grip the sutures and prevent longitudinal movement of the sutures relative to the shaft portion; and a heating element positioned within the inner shaft near the distal end of the inner shaft, the heating element being electrically coupled to the electrical power source;

wherein actuation of the trigger causes the inner shaft and the heating element to move distally relative to the outer shaft, the suture collar, and the suture holder, such that the distal end of the inner shaft moves over the suture holder and causes the second portion of the suture holder to articulate to the closed position, and such that a distal end of the heating element moves into a proximal recess in the suture holder, cuts off free ends of the held sutures, and fuses together remaining ends of the sutures within the suture holder.

* * * * *